United States Patent
Arai et al.

(10) Patent No.: US 9,615,727 B2
(45) Date of Patent: Apr. 11, 2017

(54) INSERTION APPARATUS

(71) Applicant: OLYMPUS CORPORATION, Tokyo (JP)

(72) Inventors: Keiichi Arai, Hachioji (JP); Tsugio Okazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 145 days.

(21) Appl. No.: 14/042,894

(22) Filed: Oct. 1, 2013

(65) Prior Publication Data

US 2014/0066716 A1   Mar. 6, 2014

Related U.S. Application Data

(63) Continuation of application No. PCT/JP2013/057019, filed on Mar. 13, 2013.

(30) Foreign Application Priority Data

Apr. 6, 2012   (JP) ................................ 2012-087742

(51) Int. Cl.
   *A61B 1/00* (2006.01)
   *A61B 1/005* (2006.01)
   *A61M 25/01* (2006.01)

(52) U.S. Cl.
   CPC .......... *A61B 1/0052* (2013.01); *A61B 1/0057* (2013.01); *A61M 25/0136* (2013.01); *A61M 25/0147* (2013.01)

(58) Field of Classification Search
   CPC ............................ A61B 1/0052; A61B 1/0051

USPC ..... 600/146, 148, 145, 150, 152; 604/95.04, 604/528

See application file for complete search history.

(56) References Cited

U.S. PATENT DOCUMENTS

| | | | |
|---|---|---|---|
| 5,810,715 A * | 9/1998 | Moriyama | 600/144 |
| 8,998,801 B2 * | 4/2015 | Okazaki | B25J 18/06 600/145 |
| 2006/0200000 A1 * | 9/2006 | Sato et al. | 600/146 |
| 2011/0282153 A1 * | 11/2011 | Ueki | 600/149 |

(Continued)

FOREIGN PATENT DOCUMENTS

| | | |
|---|---|---|
| EP | 2 578 139 A1 | 4/2013 |
| EP | 2 628 435 A1 | 8/2013 |

(Continued)

OTHER PUBLICATIONS

English Abstract only of WO 2011/092937 A1, dated Aug. 4, 2011.
Extended Supplementary European Search Report dated Jul. 30, 2015 from related European Application No. 13 77 1859.9.

*Primary Examiner* — Matthew J Kasztejna
*Assistant Examiner* — Rynae Boler
(74) *Attorney, Agent, or Firm* — Scully, Scott, Murphy & Presser, P.C.

(57) ABSTRACT

An insertion portion, a bending portion, an inner guide sheath, an operation portion, a fixing lever, a guide member, a crank member, a pair of link members, and cam members that are rotatable to a second rotation position where the cam members simultaneously press exposed sites of moving members to wall surfaces in a vertical direction, and a first rotation position where the cam members are separated from the exposed sites, by either one of opening and closing of the respective link members are included.

10 Claims, 25 Drawing Sheets

(56) References Cited

U.S. PATENT DOCUMENTS

2011/0295069 A1*  12/2011  Ouchi .......................... 600/146
2013/0096384 A1    4/2013  Arai

FOREIGN PATENT DOCUMENTS

| | | |
|---|---|---|
| JP | 64-005522 A | 1/1989 |
| JP | 04-102433 A | 4/1992 |
| JP | 10-151107 A | 6/1998 |
| JP | 2001-037703 A | 2/2001 |
| JP | 2005-185526 A | 7/2005 |
| JP | 2008-253744 A | 10/2008 |
| JP | 4856289 B2 | 1/2012 |
| JP | 5153970 B2 | 2/2013 |
| WO | WO 2012/120955 A1 | 9/2012 |

\* cited by examiner

INSERTION APPARATUS

CROSS REFERENCE TO RELATED APPLICATION

This application is a continuation application of PCT/JP2013/057019 filed on Mar. 13, 2013 and claims benefit of Japanese Application No. 2012-087742 filed in Japan on Apr. 6, 2012, the entire contents of which are incorporated herein by this reference.

BACKGROUND OF THE INVENTION

1. Field of the Invention

The present invention relates to an insertion apparatus having an elongated insertion portion that is inserted into a subject, and an operation portion, wherein the insertion portion is provided with an action portion that acts by operation input from the operation portion.

2. Description of the Related Art

In recent years, insertion apparatuses that are inserted into subjects, endoscopes for example, have been widely used in medical and industrial fields.

An endoscope that is used in the medical field enables observation of an organ in a body cavity by an elongated insertion portion being inserted into the body cavity that is a subject. Further, an endoscope that is used in the medical field enables various kinds of treatments with use of a treatment instrument inserted into an insertion channel for the treatment instrument that the endoscope includes, in accordance with necessity.

Further, an endoscope that is used in the industrial field enables inspection such as observation of flaws, corrosion and the like of sites to be examined in an object, and various kinds of treatments, by an elongated insertion portion of the endoscope being inserted into the inside of a jet engine and the inside of the object such as piping of a factory.

Here, a configuration is known, in which an action portion, for example, a bending portion that is bendable in a plurality of directions is provided at the insertion portion of an endoscope.

A bending portion enhances advancability of the insertion portion in a curved portion in a conduit, and in addition, makes an observation direction of an observation optical system variable, that is provided at a distal end portion located at a distal end side in an insertion direction from the bending portion (hereinafter, simply called a distal end side).

Usually, the bending portion provided at the insertion portion of an endoscope is configured to be bendable in four directions of, for example, an up, a down, a left and a right by a plurality of bending pieces being connected along an insertion direction of the insertion portion.

More specifically, the bending portion is made bendable in any of the directions of an up, a down, a left and a right by a pulling operation being performed from the operation portion for any of four wires that are moving members that have distal ends fixed to a bending piece that is located at the most distal end side among the bending pieces, are inserted through the inside of the insertion portion, and are movable forward and rearward in the insertion direction.

Note that the reason why only the bending portion bends with pulling of the wire is that in the insertion portion, outer peripheries of the wires in the soft flexible tube portion that is located at a proximal end side in the insertion direction from the bending portion (hereinafter, simply called a proximal end side) is covered with a guide sheath or the like in a state in which a distal end and a proximal end in the insertion direction are fixed to an inside of the flexible tube portion. More specifically, this is because even if the wire is pulled, the guide sheath resists a compressive force along an extending direction of the guide sheath that is added to the guide sheath.

Incidentally, a bending portion is more capable of making small turns as a length thereof in the insertion direction formed to be shorter, namely, as a bending radius thereof is smaller. Therefore, it is advantageous because passability of the distal end portion of the insertion portion with respect to a curved portion in a conduit is enhanced, and in addition thereto, the observation optical system provided at the distal end portion can be easily moved close to a site to be examined.

This is because, for example, in the case of an endoscope for medical use, if the bending portion is formed to be long, the distal end portion hits a curved portion in the curved portion of a large intestine and a visual field is easily lost, when the endoscope is inserted into the large intestine. Namely, this is because as the bending portion is shorter, the distal end portion is less likely to hit an intestinal wall in the curved portion. Note that in order to make the length of the bending portion short, the number of bending pieces that are connected can be decreased.

Furthermore, in the case of the endoscope for medical use, the method is generally used, that linearizes a curved portion by drawing the proximal end side of an insertion portion in a state in which a distal end portion and a bending portion are hooked on tissue in a body cavity after the distal end portion passes the curved portion, and thereafter, pushes the insertion portion from the proximal end side to cause the bending portion to pass through the curved portion.

In the light of the problem as above, Japanese Patent Application Laid-Open Publication No. 2008-253744 discloses the configuration in which two bending portions are provided at the distal end side of an insertion portion as the first bending portion and the second bending portion, and by an elastic covering member having a thickness, the second bending portion is more rigid than the first bending portion in the proximal end side from the first bending portion. According to the configuration, the configuration is included, in which when a wire is pulled with a small force, only the first bending portion can be bent, and when the wire is pulled with a large force, the second bending portion as well as the first bending portion can be bent, and thereby the length of the bending portion can be made variable in accordance with a situation.

Furthermore, Japanese Patent Application Laid-Open Publication No. 2005-185526 discloses the configuration in which two shape memory alloys with rigidity increasing with supply of a current are provided along the insertion direction, in the bending portion located at the distal end side of the insertion portion.

In the configuration, when only the distal end side of the bending portion is desired to be bent on one hand, a current is supplied to the shape memory alloy located at the proximal end side to enhance rigidity of the proximal end side of the bending portion, whereby the proximal end side of the bending portion is not bent, but only the distal end side is bent, with pulling of a wire. On the other hand, when the bending portion is desired to be bent from the proximal end side, a current is supplied to the shape memory alloy located at the distal end side to enhance rigidity of the distal end side of the bending portion, whereby the distal end side of the bending portion is not bent, but only the proximal end side is bent, with pulling of the wire.

Further, Japanese Patent Publication No. 4856289 discloses in the configuration provided with the first bending portion and the second bending portion at the distal end side of the insertion portion, the configuration in which the outer peripheries of four wires inserted through the inside of the insertion portion are respectively covered with inner guide sheaths that are moving members movable forward and rearward in the insertion direction, distal ends in the insertion direction of the inner guide sheaths (hereinafter, simply called distal ends) are fixed to the distal end of the second bending portion, and proximal ends in the insertion direction of the respective inner guide sheaths (hereinafter, simply called proximal ends) are simultaneously switchable to a fixed state and an unfixed state by a fixation switching member. Further, Japanese Patent Publication No. 4856289 discloses the configuration in which the outer peripheries of the respective inner guide sheaths are respectively covered with outer guide sheaths, distal ends of the outer guide sheaths are fixed to the distal end of a flexible tube portion, and the proximal ends of the outer guide sheaths are fixed to a rear side from a proximal end of the flexible tube portion.

The fixation switching member described in Japanese Patent Publication No. 4856289 is configured by a base material and two sandwiching contact members, and has a configuration that moves the two sandwiching contact members respectively in a vertical direction orthogonal to the insertion direction toward the base member with use of a link mechanism, and inserts to pinch the proximal ends of the respective inner guide sheaths in between the two sandwiching contact members and the base material to thereby fix the proximal ends of the respective inner guide sheaths.

SUMMARY OF THE INVENTION

An insertion apparatus according to one aspect of the present invention includes an insertion portion that is inserted into a subject, an action portion that is provided at the insertion portion, a moving member that is provided to move in a direction in which the insertion portion is inserted in an inside of the insertion portion, to cause the action portion to act, an operation portion that is connected to a proximal end side of the insertion portion, an operation member that is further provided at the operation portion and is for operating the action portion by an operator, a guide member that has an inner circumferential face configured by a wall surface, and through which the moving member passes along the wall surface in a direction in which the moving member moves, a crank member that has a proximal end side connected to the operation member, and has, at a distal end side, a reciprocating portion that is movable forward and rearward in the direction in which the insertion portion is inserted, with an operation of the operation member, a pair of link members that are openable and closable with a pin provided at the reciprocating portion of the crank member as a center, with movement of the crank member, a cam member that is provided in an inside of the guide member, is rotatably connected to one end of each of the link members, and is rotatable to a second rotation position where the cam member simultaneously presses exposed sites of a plurality of the moving members that penetrate through the inside of the guide member to the wall surface of the guide member in a vertical direction orthogonal to the direction in which the insertion portion is inserted, and a first rotation position where the cam member is separated from the exposed sites, by either one of opening and closing of the link member.

Further, an insertion apparatus according to another aspect includes an insertion portion that is inserted into a subject, an action portion that is provided at the insertion portion, a moving member that is provided to move in a direction in which the insertion portion is inserted in an inside of the insertion portion, to cause the action portion to act, an operation portion that is connected to a proximal end side of the insertion portion, an operation member that is further provided at the operation portion and is for operating the action portion by an operator, a guide member that has an inner circumferential face configured by a wall surface, and through which the moving member passes along the wall surface in a direction in which the moving member moves, a crank member that has a proximal end side connected to the operation member, and has, at a distal end side, a reciprocating portion that moves forward and rearward in the direction in which the insertion portion is inserted, with an operation of the operation member, a pair of link members that are openable and closable with a pin provided at the reciprocating portion of the crank member as a center, with movement of the crank member, an interposition member that is provided in an inside of the guide member, is provided inwardly of exposed sites of a plurality of the moving members that penetrate through the inside in the guide member in a vertical direction orthogonal to the direction in which the moving member moves, and has a part contactable with the exposed sites, and a cam member that is provided inwardly of the interposition member in the vertical direction, in the inside of the guide member, is rotatably connected to one end of each of the respective link members, and is rotatable to a second rotation position where the cam member simultaneously presses the exposed sites of a plurality of the moving members that penetrate through the inside of the guide member to the wall surface of the guide member in the vertical direction via the interposition member, and a first rotation position where the cam member is separated from the interposition member, by either one of opening and closing of the link member.

DETAILED DESCRIPTION OF THE PREFERRED EMBODIMENTS

Hereinafter, embodiments of the present invention will be described with reference to the drawings. Note that the drawings are schematic, attention should be paid to the fact that the relations of the thicknesses and the widths of the respective members, the ratios of the thicknesses of the respective members and the like differ from reality, and the parts in which the relations and the ratios of the dimensions differ from one another are included among the drawings as a matter of course. Note that hereinafter, an insertion apparatus will be described with an endoscope cited as an example.

(First Embodiment)

Figure 1:
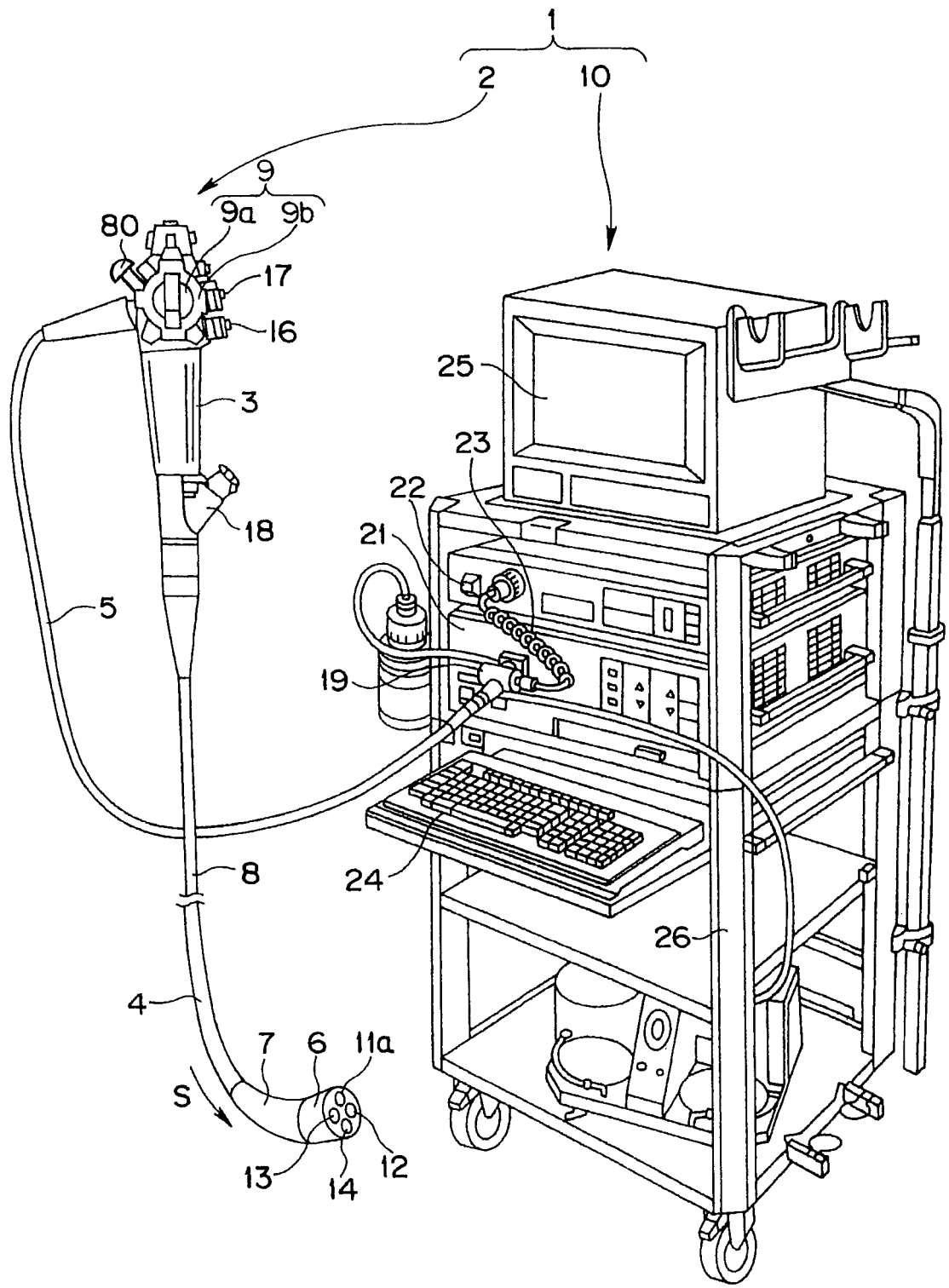
FIG. 1 is a perspective view showing a first embodiment, and an external appearance of an endoscope apparatus including an endoscope.

FIG. 1 is a perspective view showing an external appearance of an endoscope apparatus including an endoscope showing the present embodiment.

As shown in FIG. 1, an endoscope apparatus 1 has a main part configured by an endoscope 2 and a peripheral apparatus 10. The endoscope 2 has a main part configured by an insertion portion 4 that is inserted into a subject, an operation portion 3 connected to a proximal end side of the insertion portion 4, a universal cord 5, and a connector 19.

The peripheral apparatus 10 has a main part configured by a light source apparatus 21, a video processor 22, a connection cable 23, a keyboard 24, and a monitor 25, that are disposed on a rack 26. Further, the endoscope 2 and the peripheral apparatus 10 that have the configurations as above are connected to each other by the connector 19.

The operation portion 3 of the endoscope 2 is provided with a bending operation knob 9 that is another operation member, an air/water feeding operation button 16, a suction operation button 17, a treatment instrument insertion port 18, and a rotatable fixing lever 80 that is an operation member. Note that the bending operation knob 9 is configured by an up-and-down bending operation knob 9a and a left-and-right bending operation knob 9b.

The insertion portion 4 of the endoscope 2 is configured by a distal end portion 6, a bending portion 7 that is an action portion connectively provided at a proximal end side of the distal end portion 6 and is bendable in a plurality of directions, and a flexible tube portion 8 connectively provided at a proximal end side of the bending portion 7, in sequence from a distal end side. The insertion portion 4 is formed to be elongated along an insertion direction S.

The bending portion 7 acts, namely, bends by operation input to the bending operation knob 9 provided at the operation portion 3. The bending portion 7 is bendable in four directions of, for example, an up, a down, a left and a right, with pulling/slackening of a wire 30 (see FIG. 2) that will be described later and is inserted through an inside of the insertion portion 4 by a bending operation of the bending operation knob 9.

On a distal end face of the distal end side of the distal end portion 6, an objective lens 11a in an image pickup unit not illustrated and provided in the distal end portion 6 is provided, and a distal end opening 12 of a channel not illustrated that supplies a fluid toward a site to be examined in a subject, an illuminating window 13 for illuminating an inside of the subject, and a distal end opening 14 of a treatment instrument insertion channel not illustrated are provided.

From the distal end opening 12, gas and a liquid are selectively ejected by a button operation of the air/water feeding operation button 16 of the operation portion 3. From the distal end opening 14, mucosa or the like in a body cavity is selectively recovered by a button operation of the suction operation button 17 of the operation portion 3, and in addition, various treatment instruments inserted from the treatment instrument insertion port 18 are protruded toward a site to be examined, via the treatment instrument insertion channel.

At a distal end of the universal cord 5 of the endoscope 2, the connector 19 is provided, and the connector 19 is connected to the light source apparatus 21 of the peripheral apparatus 10. The connector 19 is provided with various pipe sleeves not illustrated, and various electric contacts, and the video processor 22 is electrically connected to the connector 19 via the connection cable 23. Note that the configuration of the above described endoscope apparatus 1 is only one example, and the present embodiment is not limited to the above described configuration.

Figure 2:
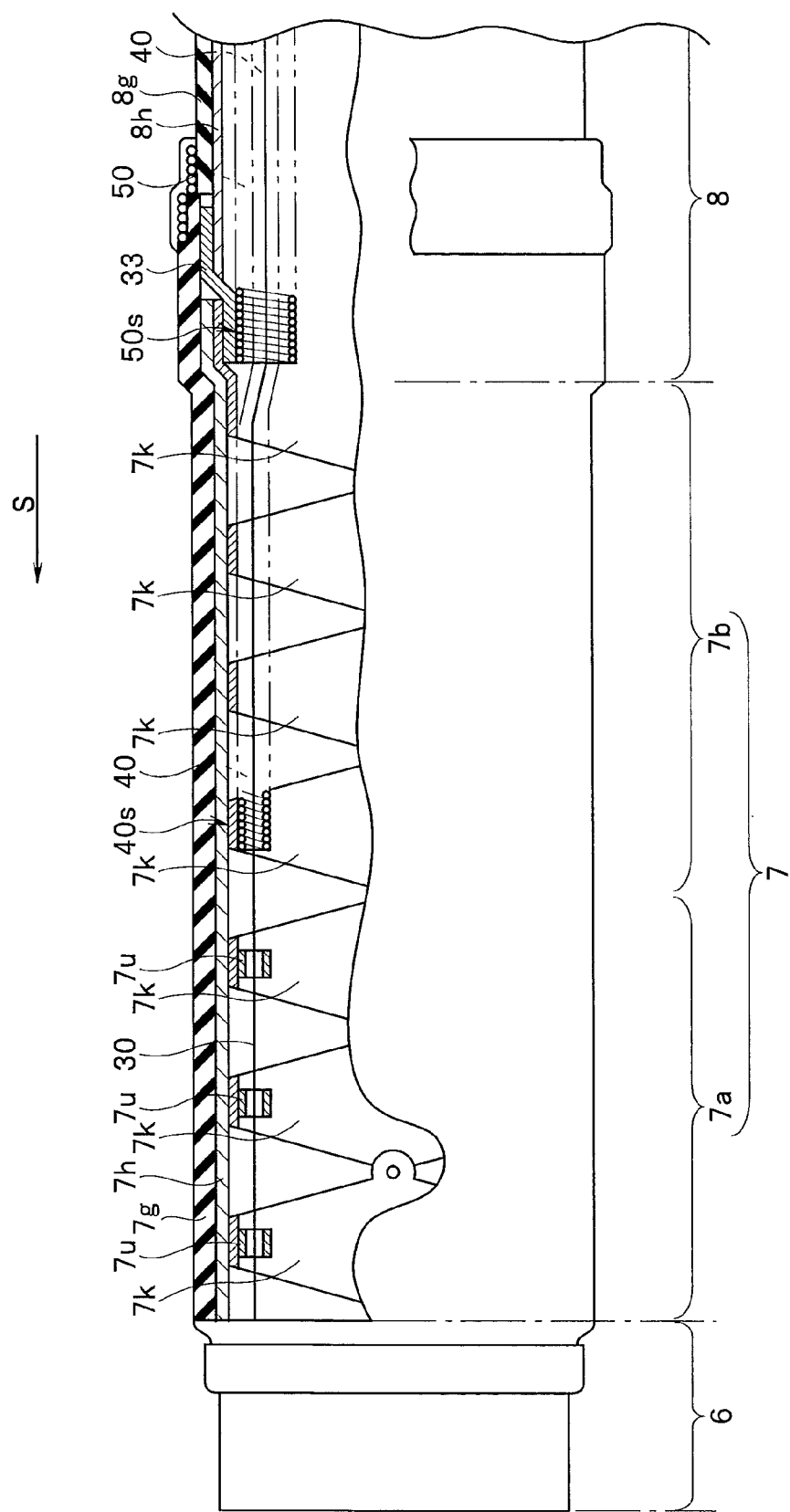
FIG. 2 is a partial sectional view schematically showing a configuration of an inside of a distal end side of an insertion portion of FIG. 1.
Figure 3:
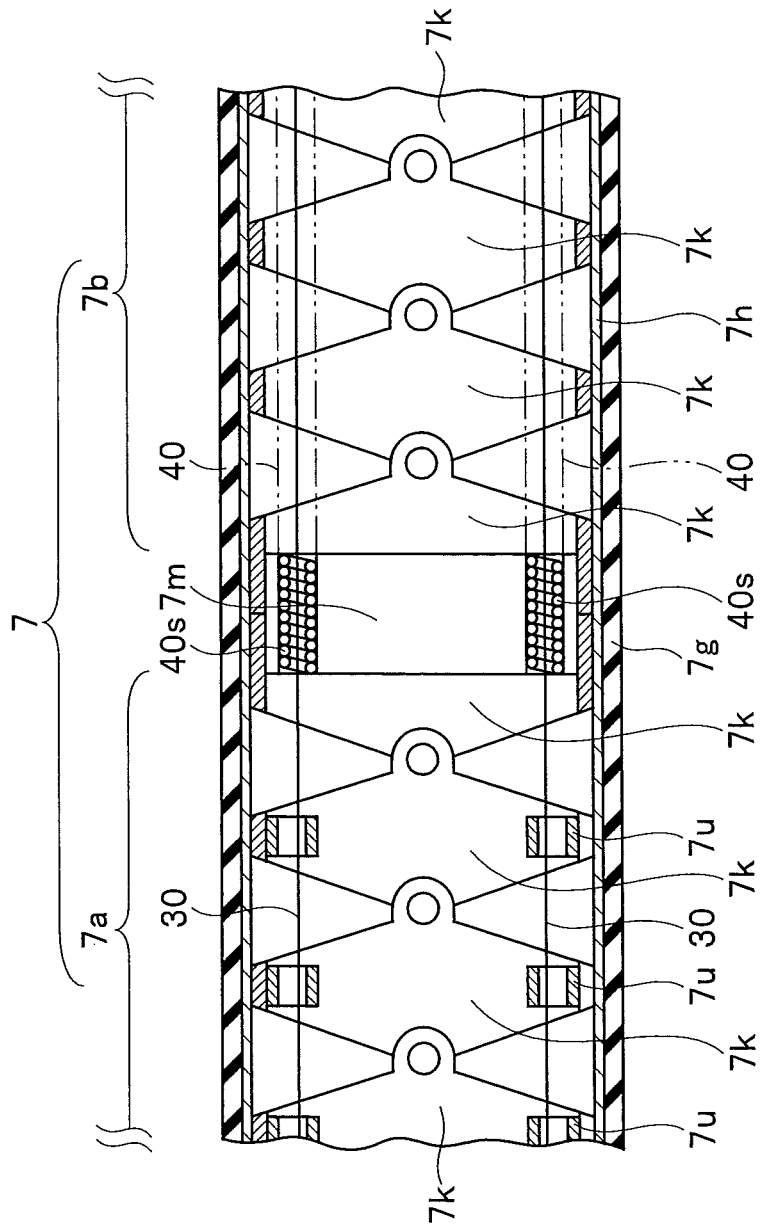
FIG. 3 is a partial sectional view showing a modification in which a first site and a second site of a bending portion of FIG. 2 are connected by a connection pipe sleeve.

Next, a configuration of an inside of the distal end side of the insertion portion 4 will be described with use of FIG. 2 and FIG. 3. FIG. 2 is a partial sectional view schematically showing the configuration of an inside of the distal end side of the insertion portion of FIG. 1, and FIG. 3 is a partial sectional view showing a modification in which a first site and a second site of the bending portion of FIG. 2 are connected by a connection pipe sleeve.

As shown in FIG. 2, in an inside of the bending portion 7, a plurality of bending pieces 7k are provided by being connected along the insertion direction S. Further, outer peripheries of the plurality of bending pieces 7k are covered with a braid 7h, and an outer periphery of the braid 7h is covered with a bending rubber 7g.

Note that hereinafter, of the bending portion 7, a site that is located in a front half portion in the insertion direction S will be called a first site 7a, and a site that is located in a rear half portion in the insertion direction S will be called a second site 7b.

For example, the four wires 30 that make an action state of the bending portion 7 variable, namely, cause the bending portion 7 to bend, and are movable forward and rearward in the insertion direction S (hereinafter, simply called forward and rearward) are inserted through insides of the operation portion 3 and the insertion portion 4 by being shifted by substantially 90° in a circumferential direction of the insertion portion 4 from one another. A plurality of bending pieces 7k that are located in the first site 7a are respectively provided with wire guides 7u that hold the four wires 30.

Further, distal ends of the respective wires 30 are fixed to the bending piece 7k that is located at the most distal end side in the insertion direction S among the plurality of bending pieces 7k.

Figure 4:
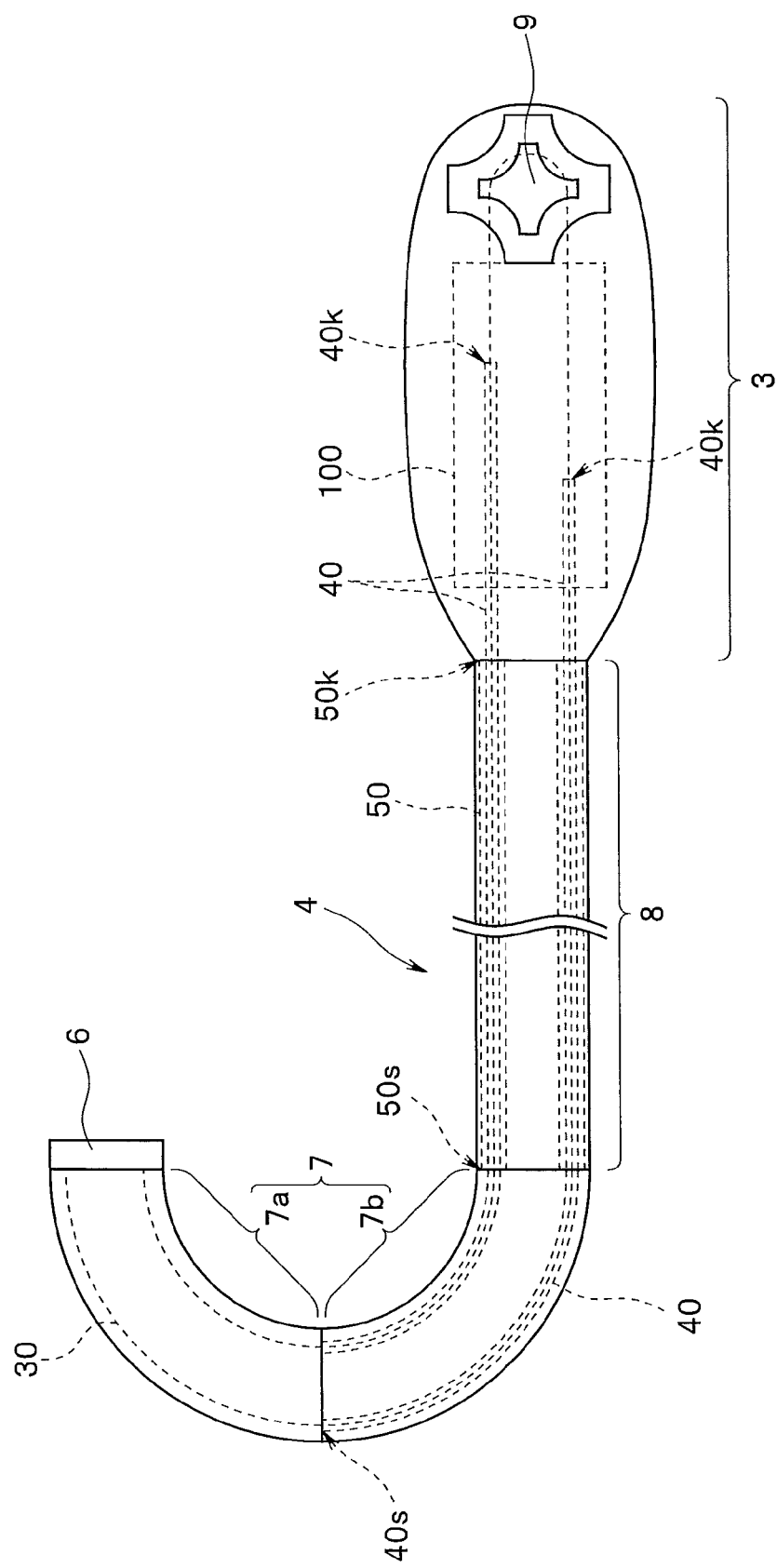
FIG. 4 is a view schematically showing a state in which the bending portion is bent from a proximal end side of the second site, in the bending portion of FIG. 2.

Furthermore, respective proximal ends of the two wires 30 for up-and-down bending are wound around a sprocket not illustrated and connected to the up-and-down bending operation knob 9a of the bending operation knob 9 as shown in FIG. 4 that will be described later. Further, respective proximal ends of the two wires 30 for left-and-right bending are wound around a sprocket that is not illustrated, is connected to the left-and-right bending operation knob 9b, and is different from the sprocket that is connected to the up-and-down bending operation knob 9a of the bending operation knob 9.

Namely, when the up-and-down bending operation knob 9a is operated, one of the two wires 30 for an up and a down is moved to a rear side in the insertion direction S (hereinafter, simply called a rear side), and the other one is moved to a front side in the insertion direction S (hereinafter, simply called a front side), namely, one is pulled and the other is slackened, whereby the bending portion 7 is bent in any one of the up and the down directions.

Further, when the left-and-right bending operation knob 9b is operated, one of the two wires 30 for a left and a right is moved to the rear side, and the other is moved to the front side. Namely, one is pulled, and the other is slackened, whereby the bending portion 7 is bent in any one of the left and the right directions.

Further, in the second site 7b, a distal end side of a connection member 33 is fixed to the bending piece 7k that is located at the most proximal end side among the plurality of bending pieces 7k, and a distal end side of a braid 8h that configures the flexible tube portion 8 is fixed to an outer periphery of a proximal end side of the connection member 33. Note that an outer periphery of the braid 8h is covered with an outer cover tube 8g.

Further, the outer peripheries of the respective four wires 30 that are inserted through the insides of the operation portion 3 and the insertion portion 4 are respectively covered with inner guide sheaths 40 that are moving members that are configured by, for example, coil pipes that are soft and elongated along the insertion direction S, and make a bending state of the bending portion variable.

Namely, in the insides of the operation portion 3 and the insertion portion 4, the respective four inner guide sheaths 40 are inserted at positions shifted in a circumferential direction of the insertion portion 4. Note that the respective inner guide sheaths 40 are formed with coil pipes of, for example, stainless steel.

Further, in the respective inner guide sheaths 40, the respective wires 30 are movable forward and rearward.

Furthermore, the reason why the respective inner guide sheaths 40 are configured by soft coil pipes is that if the outer peripheries of the respective wires 30 are covered with, for example, ordinary rigid metallic pipes, not only the bending portion 7 does not bend, but also flexibility of the flexible tube portion 8 is reduced.

Accordingly, as long as the respective inner guide sheaths 40 do not reduce bendability of the bending portion 7 and flexibility of the flexible tube portion 8, and can resist a compressive force that works along the extending direction of the respective inner guide sheaths 40 at a time of bending of the bending portion 7, members configuring the respective inner guide sheaths 40 are not limited to the coil pipes.

Further, as shown in FIG. 2, distal ends 40s of the respective inner guide sheaths 40 are fixed to the braid 7h by, for example, brazing, in an intermediate position in the insertion direction S of the bending portion 7, for example, a distal end position of the second site 7b.

Note that proximal ends 40k of the respective inner guide sheaths 40 are configured to be switchable between a fixed state and an unfixed state by a moving member fixing mechanism 100 (see FIG. 4) that is provided in the operation portion 3 and will be described later. Namely, the moving member fixing mechanism 100 fixes movement in the insertion direction S of the respective inner guide sheaths 40. Note that explanation of the moving member fixing mechanism 100 will be described later.

Further, as shown in FIG. 2, the outer peripheries of the four inner guide sheaths 40 that are located in the flexible tube portion 8 are respectively covered with outer guide sheaths 50 configured by, for example, flexible coil pipes. Note that the respective inner guide sheaths 40 that are inserted through insides of the respective outer guide sheaths 50 are made to freely advance and retract with respect to the insertion direction S. Further, the respective outer guide sheaths 50 are also formed from coil pipes of, for example, stainless steel.

Further, the outer peripheries of all of the four inner guide sheaths 40 do not have to be covered with the respective outer guide sheaths 50, and for example, only the outer periphery of the inner guide sheath 40 with which the outer periphery of the wire 30 that causes the bending portion 7 to bend in the up direction may be covered with the outer guide sheath 50. In this case, in the three inner guide sheaths 40 that are not covered with the outer guide sheaths 50, the distal ends 40s and the proximal ends 40k need to be respectively fixed.

Note that if the wire 30 is doubly covered with the coil sheath used in the conventional apparatus, flexibility of the flexible tube portion 8 is reduced. Therefore, for the inner and the outer coil sheaths, wall thicknesses and materials of the coil sheaths, and sectional shapes of elemental wires are contrived so that the inner and the outer coil sheaths both resist the pulling force of the wire 30 and are not buckled by the compressive force that bends the bending portion 7, and the flexibility of the flexible tube portion 8 is not reduced to a large extent even though the inner and the outer coil sheaths are placed in a double layer, and the inner and the outer coil sheaths are formed from a soft material.

Accordingly, the members that configure the respective outer guide sheaths 50 are not limited to the coil pipes if only the respective outer guide sheaths 50 do not reduce the flexibility of the flexible tube portion 8, and can resist the compressive force that works in the extending direction of the respective outer guide sheaths 50 at the time of bending of the bending portion 7.

Further, as shown in FIG. 2, distal ends 50s of the respective outer guide sheaths 50 are fixed to the distal end of the flexible tube portion 8, more specifically, the proximal end side of the connection member 33 by, for example, brazing. Proximal ends 50k of the respective outer guide sheaths 50 are fixed to a stop member 105 (see FIG. 7) that is located at a rear side from the flexible tube portion 8 and will be described later by, for example, brazing.

As above, the respective outer guide sheaths 50 are inserted through the inside of the flexible tube portion 8 in a state in which the distal ends 50s and the proximal ends 50k (see FIG. 7) are fixed, whereby when any one of the four wires 30 is pulled to cause the bending portion 7 to bend, the respective outer guide sheaths 50 resist the compressive force that works on the flexible tube portion 8 along the extending direction of the outer guide sheaths 50. Thereby, the flexible tube portion 8 having flexibility is prevented from bending together with the bending portion 7.

Note that in the state in which the distal ends 50s and the proximal ends 50k of the respective outer guide sheaths are fixed, the respective inner guide sheaths 40 has the distal ends 40s fixed to the distal end of the second site 7b, and has the proximal ends 40k formed along the insertion direction S to have such lengths as not to be drawn to the distal end side from the proximal ends 50k of the respective outer guide sheaths 50.

Further, as shown in FIG. 3, the bending portion 7 may have a configuration in which the first site 7a and the second site 7b are connected along the insertion direction S by a connection pipe sleeve 7m.

More specifically, the bending portion 7 may have a configuration in which the bending piece 7k that is located at the most proximal end side in the first site 7a, and the bending piece 7k that is located at the most distal end side in the second site 7b are fitted onto the connection pipe sleeve 7m the outside diameter of which is smaller than inside diameters of the respective bending pieces 7k, whereby the first site 7a and the second site 7b are connected via the connection pipe sleeve 7m.

Note that in the bending piece 7k that is located at the most proximal end side of the first site 7a, and the bending piece 7k that is located at the most distal end side of the second site 7b, holes not illustrated are respectively formed, and the respective pieces 7k are fastened via the holes to a screw hole that is not illustrated and is provided in the connection pipe sleeve 7m via a screw or the like not illustrated.

Further, in the configuration shown in FIG. 3, the distal ends 40s of the four inner guide sheaths 40 are fixed to the connection pipe sleeve 7m by, for example, brazing or the like.

According to the configuration shown in FIG. 3 as above, when the distal ends 40s of the respective inner guide sheaths 40 are joined to the intermediate position of the bending portion 7, the distal ends 40s can be joined to the connection pipe sleeve 7m, and therefore, assemblability is enhanced, as compared with the configuration of FIG. 2.

Figure 5:
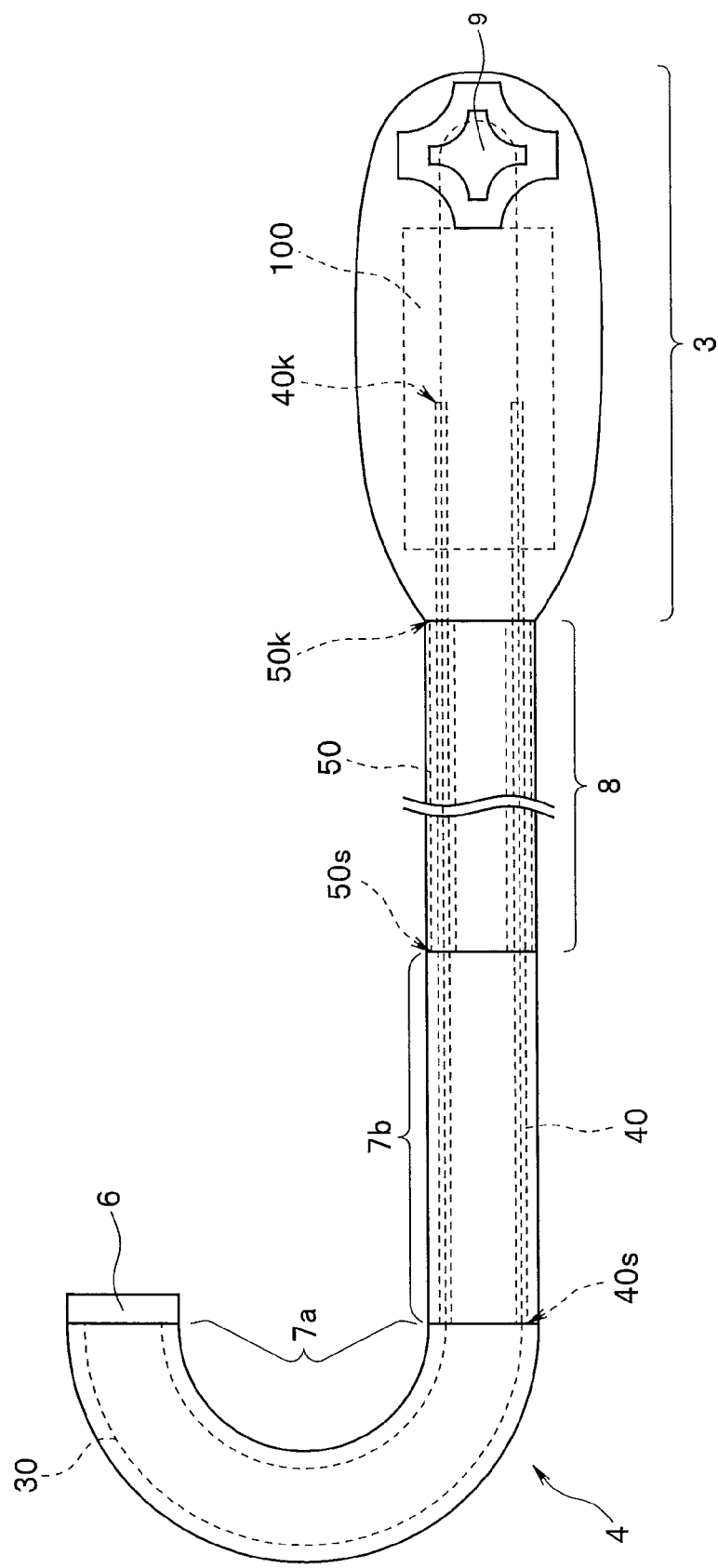
FIG. 5 is a view schematically showing a state in which the bending portion is bent from a proximal end side of the first site, in the bending portion of FIG. 2.
Figure 6:
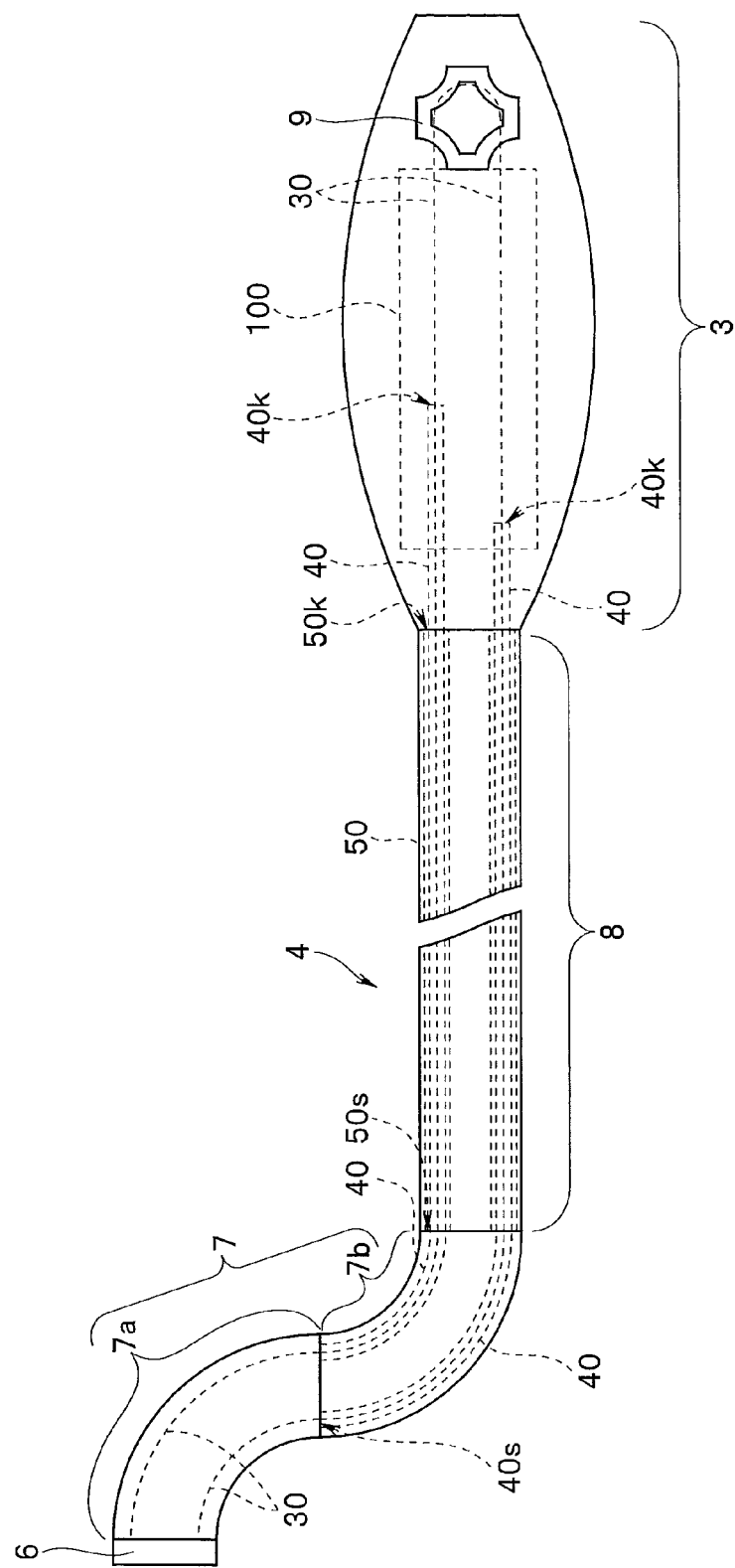
FIG. 6 is a view schematically showing a state in which proximal ends of inner guide sheaths of FIG. 4 are fixed, and the first site of the bending portion of FIG. 4 is bent to an opposite side from a bending direction of the second site.

Next, with use of FIG. 4 to FIG. 6, a bending action of the bending portion of FIG. 2 will be described. FIG. 4 is a view schematically showing a state in which the bending portion is bent from a proximal end side of the second site, in the bending portion of FIG. 2. FIG. 5 is a view schematically showing a state in which the bending portion is bent from a proximal end side of the first site, in the bending portion of FIG. 2. Further, FIG. 6 is a view schematically showing a state in which proximal ends of inner guide sheaths of FIG. 4 are fixed, and the first site of the bending portion of FIG. 4 is bent to an opposite side from a bending direction of the second site.

First, when the bending portion 7 is desired to be bent from the proximal end side of the second site 7b, namely, when the entire bending portion 7 is desired to be bent, an operator does not perform a rotational operation of the fixing lever 80, and releases fixation of the proximal ends 40k of the respective inner guide sheaths 40, using the moving member fixing mechanism 100.

In the above state, the operator operates any one of the up-and-down bending operation knob 9a and the left-and-right bending operation knob 9b, of the bending operation knob 9, and pulls any wire 30 out of the four wires 30. As a result, the respective inner guide sheaths 40 cannot resist the compressive force that acts along the extending direction of the respective inner guide sheaths 40 in the second site 7b of the bending portion 7, because the proximal ends 40k are not fixed, and the proximal ends 40k moves rearward.

Further, in the inside of the flexible tube portion 8, the respective outer guide sheaths 50 resist the compressive force that acts along the extending direction of the respective outer guide sheaths 50, because in the respective outer guide sheaths 50, the distal ends 50s and the proximal ends 50k are fixed.

As a result, as shown in FIG. 4, in the bending portion 7, the first site 7a and the second site 7b bend from the proximal end side of the second site 7b with the distal ends of the respective outer guide sheaths 50 as a starting point. Namely, the entire bending portion 7 bends.

Next, when only the first site 7a is desired to be bent in the bending portion 7, the operator performs a rotational operation of the fixing lever 80, and fixes the proximal ends 40k of the respective inner guide sheaths 40 by using the moving member fixing mechanism 100.

In the above state, when the operator operates any one of the up-and-down bending operation knob 9a and the left-and-right bending operation knob 9b of the bending operation knob 9, and pulls any wire 30 of the four wires 30, the respective inner guide sheaths 40 resist the compressive force that acts along the extending direction of the respective inner guide sheaths 40 in the second site 7b of the bending portion 7, because in the respective inner guide sheaths 40, the proximal ends 40k are fixed.

As a result, as shown in FIG. 5, in the bending portion 7, only the first site 7a bends from the proximal end side of the first site 7a with the distal ends of the respective inner guide sheaths 40 as a starting point.

Further, as shown in FIG. 4, when the up-and-down bending operation knob 9a is operated, and any one of the four wires 30, for example, the wire 30 at the upper side is pulled, in the unfixed state of the proximal ends 40k of the respective inner guide sheaths 40, the first site 7a and the second site 7b bend to the upper side as described above. Thereafter, when the first site 7a is desired to be bent in a different direction from the second site 7b, the operator rotationally operates the fixing lever 80 to fix the proximal ends 40k of the respective inner guide sheaths 40 by the moving member fixing mechanism 100.

Thereafter, when the operator operates the up-and-down bending operation knob 9a, and pulls the wire 30 at the lower side, only the first site 7a bends to the lower side opposite from the upper side, from the proximal end side, in a state in which a bending shape to the upper side of the second site 7b is fixed, because the proximal end 40k is fixed, as shown in FIG. 6.

Note that the bending direction is not limited to the upper side and the lower side, namely, in a state in which the second site 7b bends to the upper side, the corresponding wire 30 is pulled, whereby the first site 7a may be bent to the left or the right. Further, in a state in which the second site 7b bends to any one of an up, a down, a left and a right sides, the first site 7a may be bent to any one of the upper, the lower, the left and the right sides that is different from the bending direction of the second site 7b.

Namely, the endoscope 2 of the present embodiment has the configuration in which the first site 7a and the second site 7b can be bent in different directions. Note that the first site 7a and the second site 7b can be bent in different directions, whereby such an effect can be expected that observation and treatment are easily performed in the locations where lesions are difficult to see from in front, such as the cardia of a stomach, the vicinity of the back of an anal of a rectum, and the back of a fold of a large intestine, and in addition, a surgeon can easily perform a bending operation with only one hand.

From the above, fixing and unfixing of the proximal ends 40k of the respective inner guide sheaths 40 are switched, and thereby the bending state of the bending portion 7 can be switched.

Figure 7:
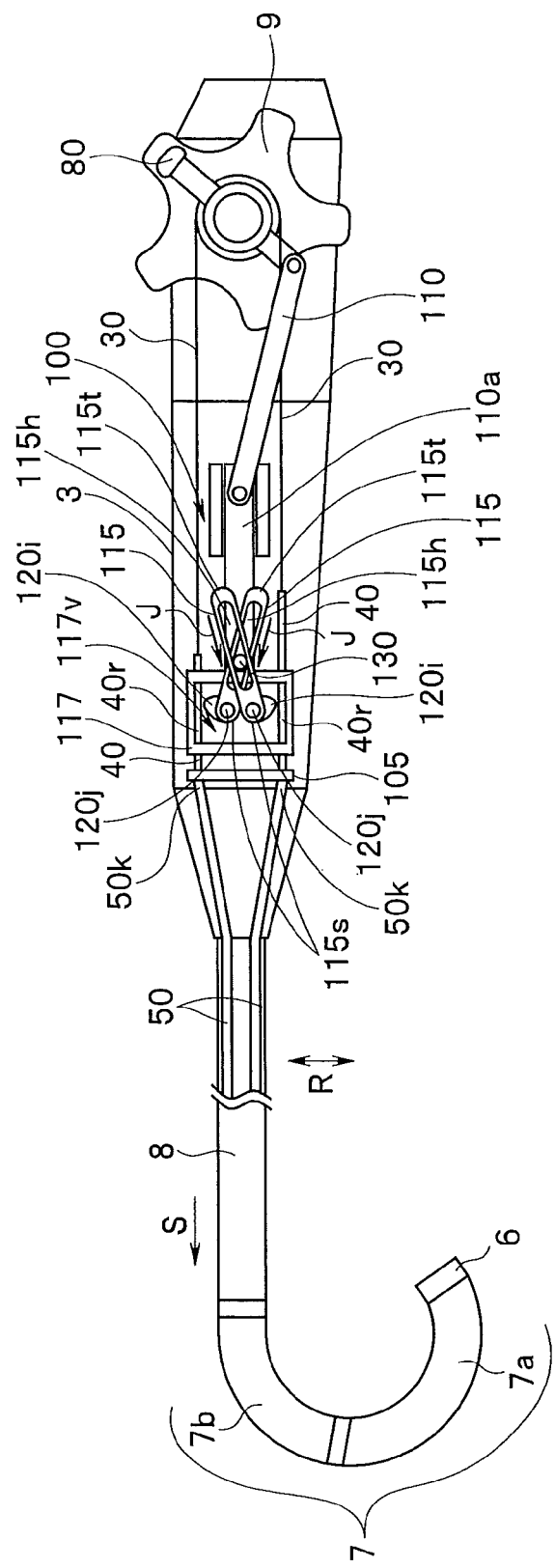
FIG. 7 is a view schematically showing a configuration in which a moving member fixing mechanism is provided in an operation portion of the endoscope of FIG. 1 with the insertion portion and the operation portion of the endoscope in a state in which the inner guide sheaths are unfixed by the moving member fixing mechanism.
Figure 8:
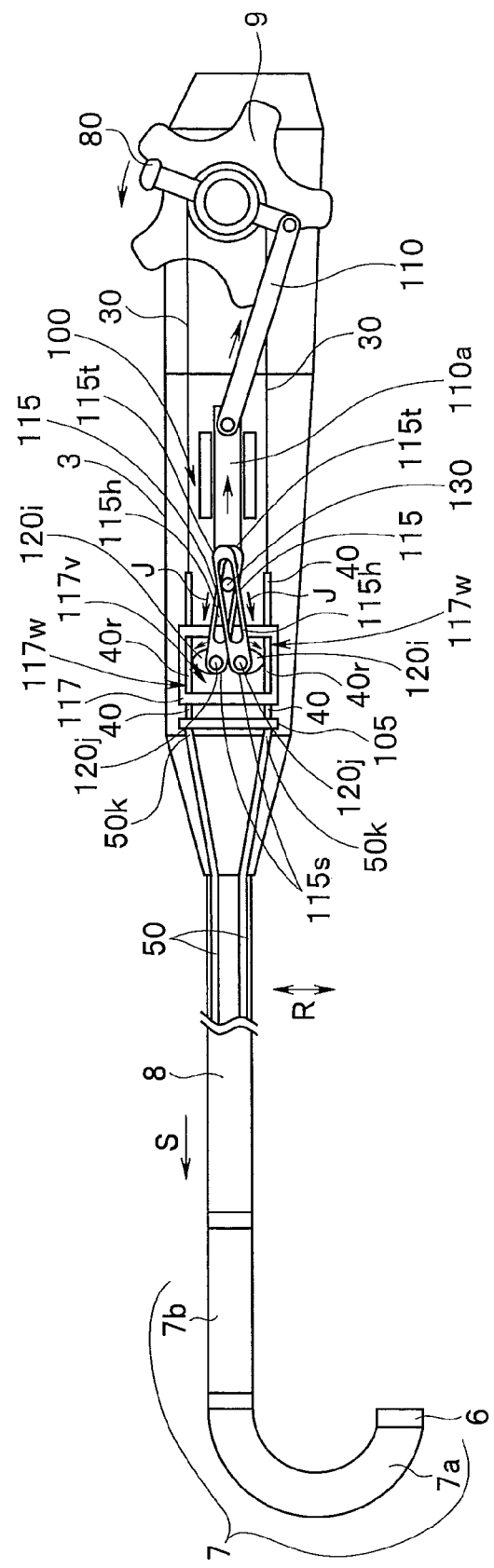
FIG. 8 is a view schematically showing a state in which the inner guide sheaths are fixed by the moving member fixing mechanism of FIG. 7 with the insertion portion and the operation portion of the endoscope.
Figure 9:
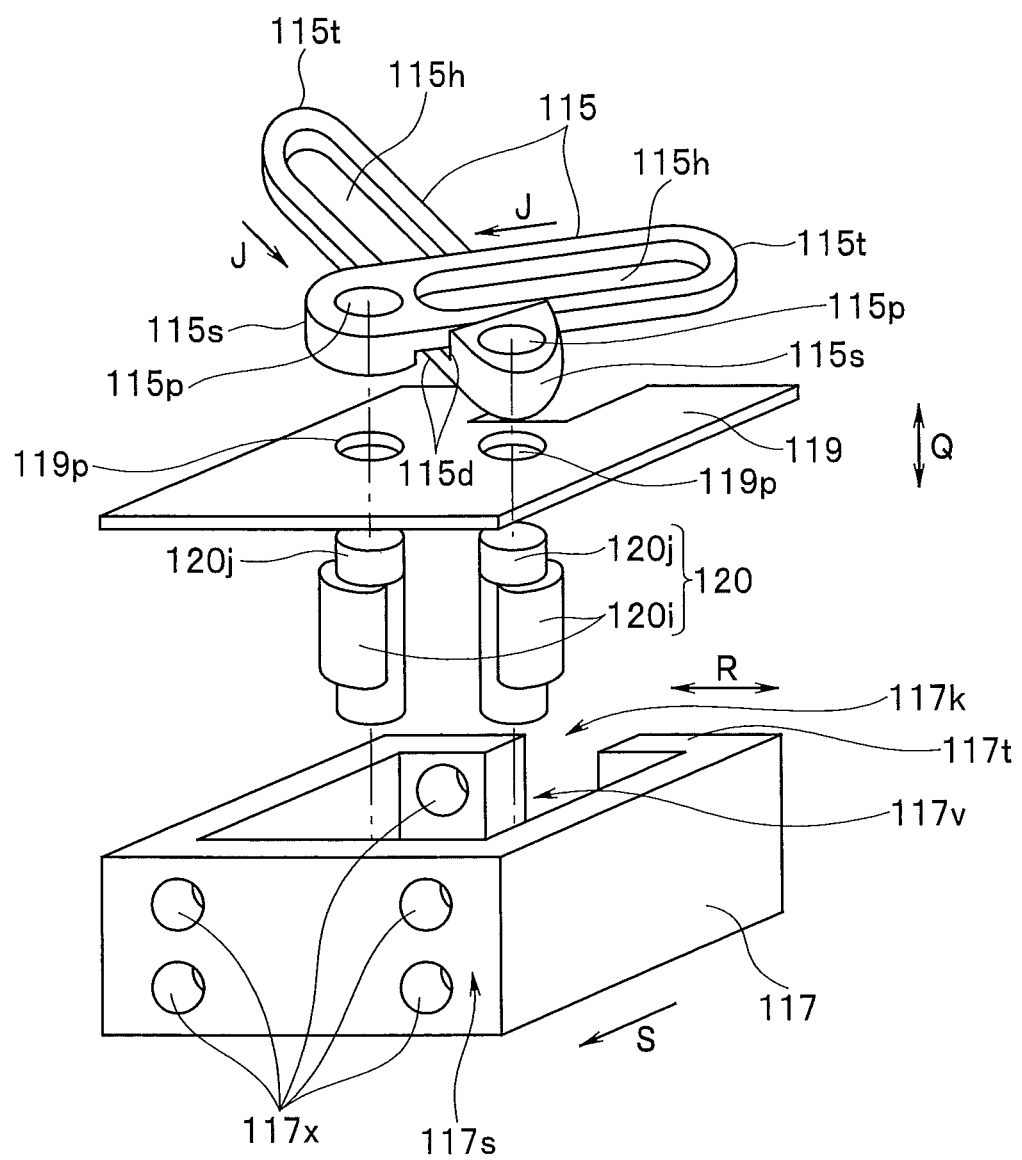
FIG. 9 is a perspective view showing a guide member, link members, a cover plate and cam members in the moving member fixing mechanism of FIG. 7 and FIG. 8 under enlargement and disassembly.

Next, the moving member fixing mechanism 100 that fixes movement of the proximal end 40k of the inner guide sheath 40 will be described with use of FIG. 7 to FIG. 9. FIG. 7 is a view schematically showing a configuration in which the moving member fixing mechanism is provided in an operation portion of the endoscope of FIG. 1 with the insertion portion and the operation portion of the endoscope in a state in which the inner guide sheaths are unfixed by the moving member fixing mechanism. FIG. 8 is a view schematically showing a state in which the inner guide sheaths are fixed by the moving member fixing mechanism of FIG. 7 with the insertion portion and the operation portion of the endoscope. FIG. 9 is a perspective view showing a guide member, link members, a cover plate and cam members in the moving member fixing mechanism of FIG. 7 and FIG. 8 under enlargement and disassembly.

As shown in FIG. 7 and FIG. 8, in the operation portion 3, the moving member fixing mechanism 100 that simultaneously fixes movement in the insertion direction S of the proximal end 40k sides of the respective inner guide sheaths 40 is provided. Note that hereinafter, the case in which the moving member fixing mechanism 100 simultaneously fixes the proximal end 40k sides of all the four inner guide sheaths 40 is shown as an example, but the moving member fixing mechanism 100 is not limited thereto, and the number of the inner guide sheaths 40 that are simultaneously fixed may be any number if only the number is two or more.

The moving member fixing mechanism 100 has a main part configured by including a crank member 110, a pair of link members 115, a guide member 117 and a cam member 120.

The crank member 110 has a proximal end connected to an end portion in the operation portion 3, of the fixing lever 80, and has, at a distal end side, a reciprocating portion 110a that is movable forward and rearward with a rotational operation of the fixing lever 80, and is elongated along the insertion direction S. Namely, the crank member 110 has a function of converting rotation of the fixing lever 80 into a reciprocating motion of the reciprocating portion 110a in the insertion direction S.

At a distal end of the reciprocating portion 110a of the crank member 110, a screw hole not illustrated is formed, and to the screw hole, a slider pin 130 movable forward and rearward with the reciprocating portion 110a is fixed.

The pair of link members 115 are formed into the same shapes respectively, and cross each other in a shape of X to be openable and closable.

More specifically, as shown in FIG. 9, the pair of link members 115 have cutouts 115d formed from vicinities of distal ends 115s that are one ends to proximal ends 115t that are the other ends, along an axial direction J, on one surfaces of the respective link members 115. The pair of link members 115 cross each other in the shape of X so that the cutouts 115d of the respective link members 115 face each other and are superimposed on each other in a direction Q.

Accordingly, top surfaces and bottom surfaces in FIG. 9 in the direction Q of the respective link members 115 crossing each other in the shape of X are respectively located at the same height, because the cutouts 115d face each other and are superimposed on each other in the direction Q.

Further, in the respective link members 115, elongated long holes 115h are formed along the axial direction J of the link members 115 to have the same shapes. The slider pin 130 is fitted into crossing sites of the respective long holes 115h so as to penetrate through both the long holes 115h in the direction Q.

Accordingly, by the rotational operation of the fixing lever 80, the crossing sites of the pair of link members 115 also move forward and rearward as shown in FIG. 7 and FIG. 8 by forward and rearward movement of the slider pin 130 in the long holes 115h with forward and rearward movement of the reciprocating portion 110a of the crank member 110.

Thereby, as shown in FIG. 7 and FIG. 8, the pair of link members 115 is openable and closable with the slider pin 130 as a center. More specifically, as shown in FIG. 7, if the slider pin 130 is located at a front side, namely, located at the distal end 115s sides, in the crossing sites of the respective long holes 115h, a crossing angle of the respective long holes 115h is large, and the pair of link members 115 are opened. Further, as shown in FIG. 8, when the slider pin 130 is located at a rear side, namely, located at the proximal end 115t sides in the crossing sites of the respective long holes 115h, the crossing angle of the respective long holes 115h becomes smaller than that of FIG. 7, and the pair of link members 115 are closed. Note that the crossing angle refers to an angle that connects the slider pin 130, and rotational centers of camshafts 120j that will be described later of the respective cam members 120.

Further, the distal end 115s sides of the pair of link members 115 are located in a space 117v in the guide member 117 the planar shape of which is a C-shape. Note that the guide member 117 is fixed to a structure body not illustrated in the operation portion 3.

More specifically, a cutout 117k (see FIG. 9) is formed in a substantial center in the vertical direction R orthogonal to the insertion direction S and the direction Q of a proximal end side site 117t of the guide member 117, whereby the planar shape of the guide member 117 has a C-shape. Further, the distal end 115s sides of the pair of link members 115 are located in the space 117v via the cutout 117k.

As shown in FIG. 9, in the guide member 117, two through-holes 117x that penetrate through the space 117v along the insertion direction S are formed near each of one end and the other end in the vertical direction R in each of the distal end side site 117s and the proximal end side site 117t. Namely, four of the through-holes 117x are formed in each of the distal end side site 117s and the proximal end side site 117k.

Note that proximal end 40k sides of the inner guide sheaths 40 are penetrated along the insertion direction S through the respective through-holes 117x as shown in FIG. 7 and FIG. 8. More specifically, the inner guide sheaths 40 with the wires 30 for bending the bending portion 7 up and down, for example, being inserted through insides thereof are respectively penetrated through the two through-holes 117x formed along the direction Q at one end side in the vertical direction R. Further, the inner guide sheaths 40 with the wires 30 for bending the bending portion 7 to the left and the right, for example, being inserted through inside thereof are respectively penetrated through the two through-holes 117x formed along the direction Q at the other end side in the vertical direction R.

Accordingly, after the respective inner guide sheaths 40 are penetrated, sites of the respective inner guide sheaths 40 that are located in the space 117v are exposed to the space 117v.

In the space 117v, upper ends in the direction Q of the camshafts 120j of the respective cam members 120 are respectively connected to respective through-holes 115p that are formed to penetrate in the direction Q for the distal ends 115s of the respective link members 115 to be rotatable via respective through-holes 119p that are formed in a cover 119 that closes a top surface of the guide member 117. Note that lower ends in the direction Q of the respective camshafts 120j are respectively connected to a bottom surface of the guide member 117 or a structure body not illustrated in the operation portion 3 to be rotatable.

In outer circumferential faces of the respective camshafts 120j in the space 117v, eccentric cams 120i that respectively have the same shapes are respectively provided at sites that face in the vertical direction R to respective exposed sites 40r that are exposed in the space 117v in the proximal end 40k sides of the four inner guide sheaths 40 that are inserted through the through-holes 117x.

Note that since in a space in the direction Q between the respective eccentric cams 120i and the pair of link members 115, the aforementioned cover 119 is located, the respective eccentric cams 120i in the space 117v are made invisible from above in the direction Q due to the cover 119.

The respective eccentric cams 120i rotate with the respective camshafts 120j by opening and closing of the pair of link members 115 as shown in FIG. 7 and FIG. 8. For example, in an opened state of the pair of link members 115 shown in FIG. 7, namely, when the crossing angle of the respective long holes 115h is large due to forward movement of the slider pin 130, the respective eccentric cams 120i rotate clockwise with the respective camshafts 120j to be located in a first rotation position where the respective eccentric cams 120i separate from the respective exposed sites 40r by such a predetermined distance that does not inhibit movement in the insertion direction S of the inner guide sheaths 40. Namely, when the respective eccentric cams 120i are located in the first rotation position, the proximal end 40k sides of the respective inner guide sheaths 40 are movable forward and rearward.

Further, in a closed state of the pair of link members 115 shown in FIG. 8, namely, when the crossing angle of the respective long holes 115h is smaller than that of FIG. 7 due to rearward movement of the slider pin 130, the respective eccentric cams 120i rotate counterclockwise with the respective camshafts 120j to contact the respective exposed sites 40r. Thereby, the respective eccentric cams 120i rotate counterclockwise with the respective camshafts 120*j* to be located in a second rotation position where the respective eccentric cams 120*i* simultaneously press the respective exposed sites 40*r* in the vertical direction R to wall surfaces 117*w* that configure an inner circumferential face of the guide member 117 with which the respective exposed sites 40*r* are contactable.

Note that in the second rotation position, contact points of the respective eccentric cams 120*i* and the respective exposed sites 40*r* are points of action, the rotational centers of the respective camshafts 120*j* are fulcrums, the crossing position of the pair of link members 115 where the slider pin 130 is located is a power point, and by a lever force, the respective cam members 120 give pressing force (braking force) in the vertical direction R to the respective exposed sites 40*r*. Thereby, forward and rearward movement of the respective exposed sites 40*r* is simultaneously locked.

Note that in the second rotation position, the respective eccentric cams 120*i* each press two of the exposed sites 40*r* to the wall surface 117*w*. Namely, one of the eccentric cams 120*i* simultaneously presses the exposed sites 40*r* of the two inner guide sheaths 40 with the up and down bending wires 30 being respectively inserted through the insides thereof to the wall surface 117*w*. The other eccentric cam 120*i* simultaneously presses the exposed sites 40*r* of the two inner guide sheaths 40 with the left and right bending wires 30 being respectively inserted through the insides thereof to the wall surface 117*w*.

Further, with opening and closing of the pair of link members 115 having the same shapes, the respective eccentric cams 120*i* rotate between the second rotation position and the first rotation position in the same timing.

Next, an operation of the present embodiment will be described.

First, when the operator rotationally operates the fixing lever 80 clockwise, the reciprocating portion 110*a* of the crank member 110 moves forward in the operation portion 3. As a result, in the respective long holes 115*h*, the slider pin 130 moves forward, namely, to the distal end 115*s* sides of the pair of link members 115, whereby the crossing angle of the respective long holes 115*h* becomes large, and the crossing position of the pair of link members 115 moves to the distal end 115*s* sides. From this, as shown in FIG. 7, the respective eccentric cams 120*i* rotate clockwise to be located in the first rotation position together with the respective camshafts 120*j*, and do not give braking force to the exposed sites 40*r* of the inner guide sheaths 40.

Accordingly, as described above, when the rotational operation of the bending operation knob 9 is performed thereafter, the bending portion 7 bends from the proximal end of the second site 7*b* as shown in FIG. 7.

Next, when the operator rotationally operates the fixing lever 80 counterclockwise, the reciprocating portion 110*a* of the crank member 110 moves rearward in the operation portion 3. As a result, in the respective long holes 115*h*, the slider pin 130 moves rearward, namely, to the proximal end 115*t* sides of the pair of link members 115, whereby the crossing angles of the respective long holes 115*h* becomes smaller than that of FIG. 7, and the crossing position of the pair of link members 115 moves to the proximal end 115*t* sides. From this, as shown in FIG. 8, the respective eccentric cams 120*i* rotate counterclockwise to be located in the second rotation position together with the respective camshafts 120*j*, and press the respective exposed sites 40*r* in the vertical direction R to the wall surface 117*w*, and therefore, the respective exposed sites 40*r* are sandwiched between the respective eccentric cams 120*i* and the wall surfaces 117*w* and are simultaneously fixed. Note that in the second rotation position, the respective eccentric cams 120*i* crush contact sites to the exposed sites 40*r* which the respective eccentric cams 120*i* contact, in the vertical direction R.

Accordingly, as described above, when a rotational operation of the bending operation knob 9 is performed thereafter, the bending portion 7 bends from the proximal end of the first site 7*a*, as shown in FIG. 8.

As above, in the present embodiment, it is shown that the moving member fixing mechanism 100 provided in the operation portion 3 is configured by the crank member 110 having, at the distal end side, the reciprocating portion 110*a* movable forward and rearward, with rotation of the fixing lever 80, the pair of openable and closable link members 115 that are crossed in the X-shape, and have the long holes 115*h* in which the slider pin 130 of the reciprocating portion 110*a* is fitted in the crossing position respectively along the axial direction J, and the cam members 120 rotatably connected to the respective distal ends 115*s* of the pair of link members 115.

Further, it is shown that the eccentric cams 120*i* of the respective cam members 120 separate from the exposed sites 40*r* of the respective inner guide sheaths 40 in the first rotation position in the opened position of the pair of link members 115, whereas in the second rotation position in the closed position of the pair of link member 115, the eccentric cams 120*i* press the exposed sites 40*r* of the respective inner guide sheaths 40 to the wall surfaces 117*w* in the vertical direction R, and simultaneously fix forward and rearward movement of the respective exposed sites 40*r*.

Further, it is shown that in the second rotation position, the contact points of the respective eccentric cams 120*i* and the respective exposed sites 40*r* are the points of action, the rotational centers of the respective camshafts 120*j* are the fulcrums, and the crossing position of the pair of link members 115 where the slider pin 130 is located is the power point, and by the lever force, the respective camshafts 120*j* give the pressing force to the respective exposed sites 40*r* in the vertical direction R.

According to the above, in the second rotation position, the crossing position of the pair of link members 115 that cross each other moves rearward, and thereby a distance between the fulcrums and the power point becomes long. Thereby, a large force is given to the respective exposed sites 40*r* as braking force from the points of action, and therefore, large braking force can be given to the exposed sites 40*r* of the respective inner guide sheaths 40 with small operation force amount of the fixing lever 80. As a result, reliable simultaneous fixation of the respective exposed sites 40*r* with use of the respective eccentric cams 120*i* is enabled.

Further, a distance in the vertical direction R between a center of the camshaft 120*j* of the cam member 120 and the respective exposed sites 40*r* can be made shorter than the conventional apparatus. As a result, with the configuration of the compact moving member fixing mechanism 100, the above described braking force can be made stronger.

Further, the pair of link members 115 are crossed, whereby in the small space in the operation portion 3, more specifically, the small space 117*v* of the guide member 117, the distal end sides of the pair of link members 115 can be opened and closed at large opening and closing angles. As a result, even in the small space 117*v*, the respective eccentric cams 120*i* can be sufficiently rotated to the second rotation position from the first rotation position.

From the above, the endoscope 2 can be provided, which has the configuration that can reliably perform simultaneous fixation of a plurality of the inner guide sheaths 40 without upsizing the operation portion 3, even with the simple configuration with only the crank member 110, the pair of link members 115, the guide member 117 and the cam members 120, and a small operation force amount of the fixing lever 80.

(Second Embodiment)

Figure 10:
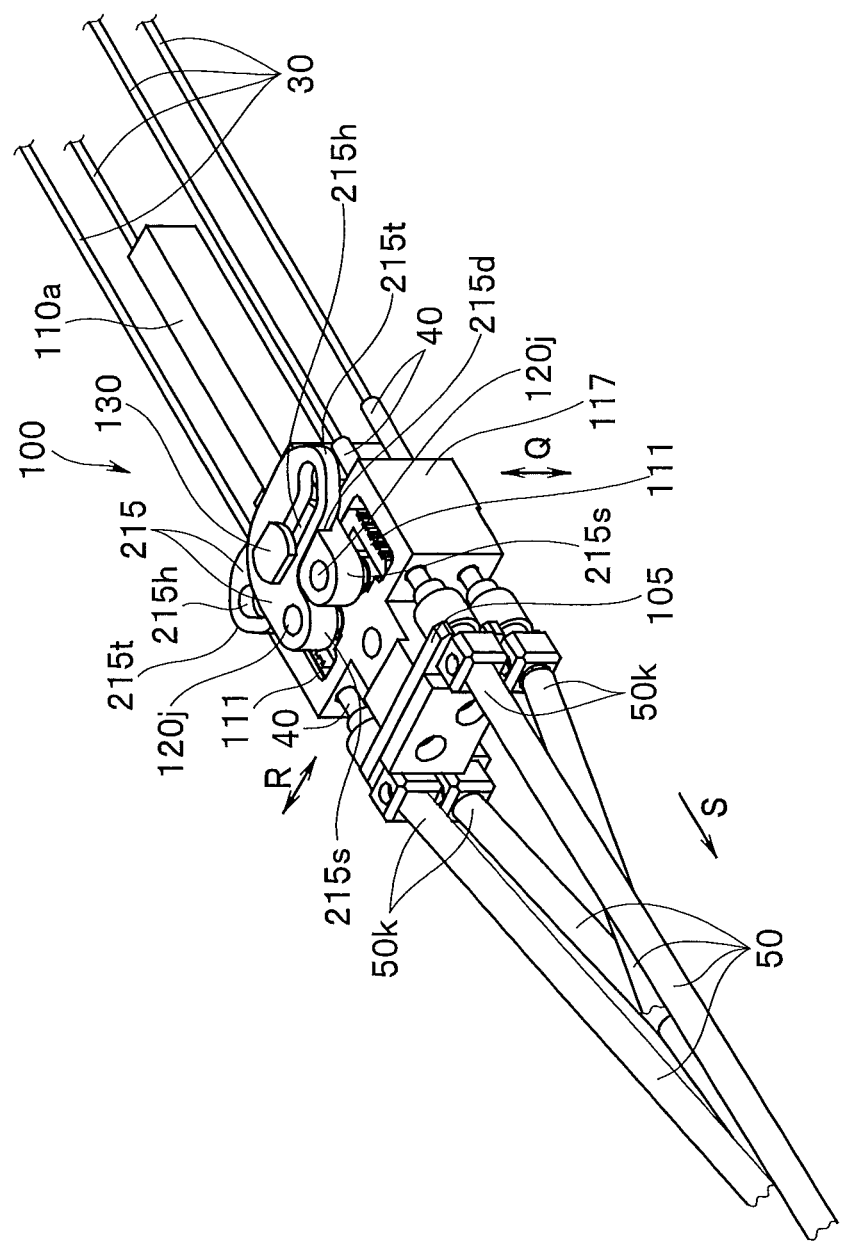
FIG. 10 is a partial perspective view showing a second embodiment and showing a moving member fixing mechanism provided in the operation portion of an endoscope with inner guide sheaths, outer guide sheaths, and wires.
Figure 11:
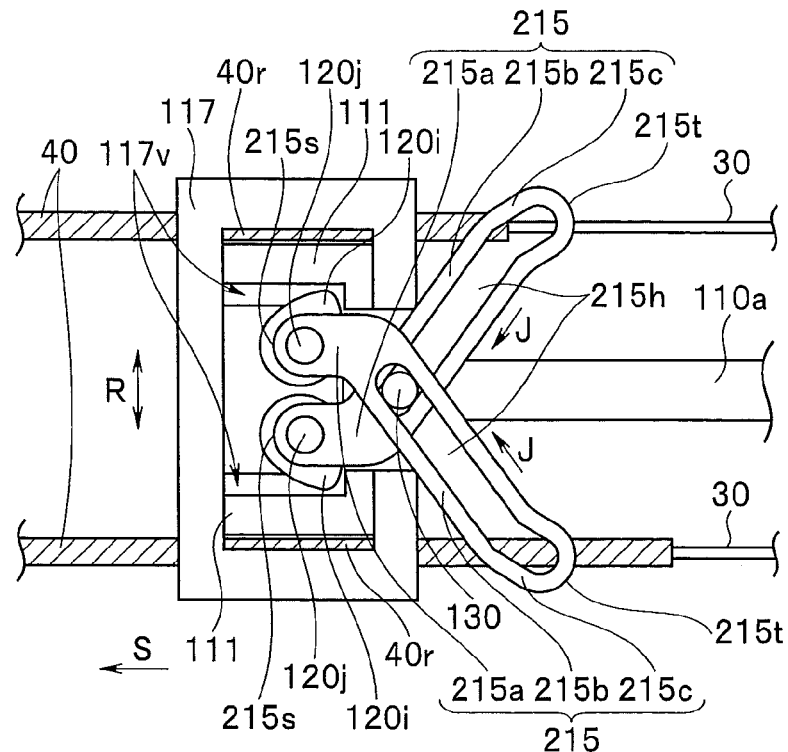
FIG. 11 is a view schematically showing a state in which the inner guide sheaths are unfixed by the moving member fixing mechanism of FIG. 10.
Figure 12:
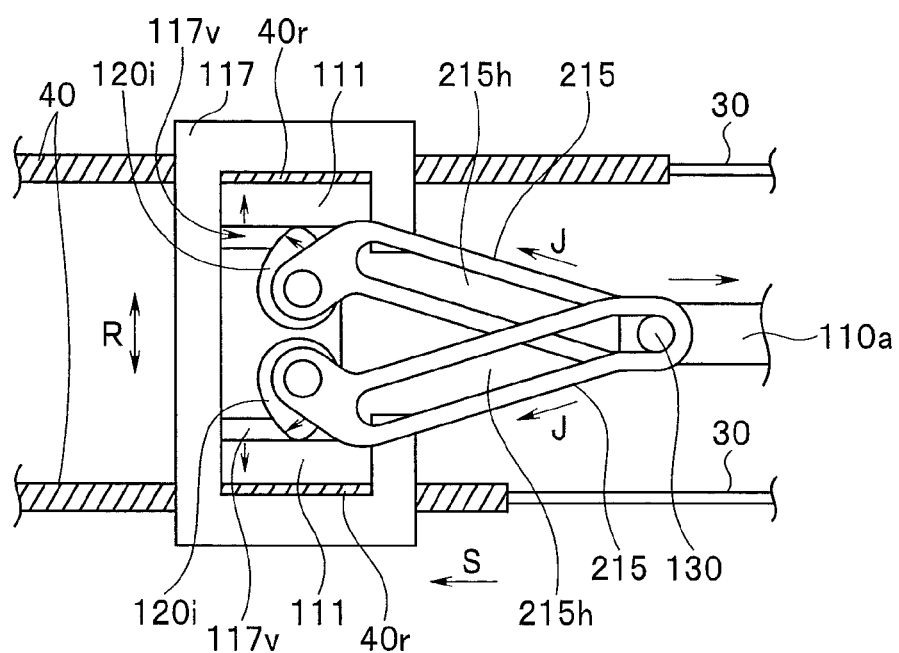
FIG. 12 is a view schematically showing a state in which the inner guide sheaths are fixed by the moving member fixing mechanism of FIG. 10.

FIG. 10 is a partial perspective view showing the present embodiment and showing a moving member fixing mechanism provided in the operation portion of an endoscope with inner guide sheaths, outer guide sheaths and wires. FIG. 11 is a view schematically showing a state in which the inner guide sheaths are unfixed by the moving member fixing mechanism of FIG. 10. FIG. 12 is a view schematically showing a state in which the inner guide sheaths are fixed by the moving member fixing mechanism of FIG. 10.

A configuration of the endoscope of the second embodiment differs in the point in which the moving member fixing mechanism is further provided with an interposition member, shapes of the pair of link members, and shapes of long holes formed in the link members, as compared with the endoscope of the first embodiment shown in FIG. 1 to FIG. 9 described above. Therefore, only the differences will be described, the same components as those in the first embodiment will be assigned with the same reference signs, and explanation thereof will be omitted.

As shown in FIG. 10 to FIG. 12, in the present embodiment, the moving member fixing mechanism 100 has a main part configured by including the crank member 110, a pair of link members 215, the guide member 117, a brake member 111 that is an interposition member, and the cam members 120. Note that in FIG. 10 to FIG. 12, the crank member 110 is shown by the other components than the reciprocating portion 110a being omitted.

As shown in FIG. 11 and FIG. 12, a pair of brake members 111 are respectively located to be contactable with the respective exposed sites 40r, in an inner side in the vertical direction R than the exposed sites 40r of the respective inner guide sheaths 40 that are located in the space 117v, more specifically, between a pair of the cam members 120 and the respective exposed sites 40r in the vertical direction R, in the space 117v in the guide member 117, in the present embodiment, and, for example, sections thereof are formed into L-shapes.

Further, in the aforementioned first rotation position of the respective cam members 120, the respective brake members 111 are separated from the respective exposed sites 40r in the vertical direction R at such predetermined distances that do not inhibit movement in the insertion direction S of the respective inner guide sheaths. Further, in the aforementioned second rotation position, the respective brake members 111 contact the respective exposed sites 40r by being pressed by the eccentric cams 120i of the respective cam members 120.

The pair of link members 215 are respectively formed into the same shapes, and cross each other in the X shape to be openable and closable in the second rotation position and the first rotation position that will be described later, with respect to the vertical direction R.

More specifically, as shown in FIG. 10, the pair of link members 215 are each formed by having a first parallel site 215a that is located at a distal end 215s side that is one end, and becomes parallel with the insertion direction S in the first rotation position shown in FIG. 11, a second parallel site 215c that is located at a proximal end 215t side that is the other end, and becomes parallel with the insertion direction S in the second rotation position shown in FIG. 10, and a linear connection site 215b that connects the first parallel site 215a and the second parallel site 215c, and being folded into a crank shape. Namely, the pair of link members 215 of the present embodiment are formed to be shorter in the insertion direction S and longer in the axial direction J than the link members 115 of the first embodiment by the amount of the two folded portions.

Further, on one surfaces of the respective link members 215, cutouts 215d (see FIG. 10) are formed from vicinities of the distal ends 215s to the proximal ends 215t along the axial direction J, and the pair of link members 215 cross each other in the X shape so that the cutouts 215d of the respective link members 215 face each other and are superimposed on each other in the direction Q.

Accordingly, top surfaces and bottom surfaces in FIG. 10 in the direction Q of the respective link members 215 that cross each other in the X shape are respectively located at the same height because the cutouts 215d face each other and are superimposed on each other in the direction Q.

Further, in the respective link members 215, long holes 215h are formed into such shapes that are folded at boundaries of the connection sites 215b and the second parallel sites 215c by respectively having the same shapes, along the connection sites 215b and the second parallel sites 215c, in the connection sites 215b and the second parallel sites 215c. Further, in crossing sites of the respective long holes 215h, the slider pin 130 is fitted to penetrate through both the long holes 215h in the direction Q.

Accordingly, by a rotational operation of the fixing lever 80, by forward and backward movement of the slider pin 130 in the long holes 215h with forward and backward movement of the reciprocating portion 110a of the crank member 110, the crossing sites of the pair of link members 215 also move forward and backward as shown in FIG. 11 and FIG. 12.

Thereby, as shown in FIG. 11 and FIG. 12, the pair of link members 215 are openable and closable with the slider pin 130 as a center.

More specifically, as shown in FIG. 11, when in the crossing sites of the respective long holes 215h, the slider pin 130 is located at a front side, namely, near the distal ends 215s in the first rotation position shown in FIG. 11, the crossing angle of the respective long holes 215h becomes large, and the pair of link members 215 are opened.

Further, as shown in FIG. 12, when in the crossing sites of the respective long holes 215h, the slider pin 130 is located at a rear side, namely, near the proximal ends 215t in the second rotation position shown in FIG. 12, the crossing angle of the respective long holes 215h becomes smaller than that of FIG. 11, and the respective second parallel sites 215c are superimposed on each other in the direction Q, so that the pair of link members 215 are closed.

Furthermore, since when the slider pin 130 is fitted in the long holes 215h in the respective second parallel sites 215c in the second rotation position shown in FIG. 12, the respective second parallel sites 215c are superimposed on each other in the direction Q as described above, forces that work on the respective second parallel sites 215c to open respectively are cancelled off, and therefore, movement to the distal end 215s sides, of the slider pin 130 in the respective long holes 215h is fixed. Namely, since the closed state of the pair of link members 215 is fixed, the rotation position of the fixing lever 80 is fixed.

Further, the distal end 215s sides of the pair of link members 215 are located in the space 117v in the guide member 117.

Further, in the present embodiment, the respective cam members 120 are respectively connected to the distal ends 215s of the respective link members 215 to be rotatable in the space 117v.

Further, the eccentric cams 120i of the respective cam members 120 are respectively provided at sites that face the respective brake members 111 in the vertical direction R, in the outer circumferential faces of the respective camshafts 120j in the space 117v.

The respective eccentric cams 120i rotate with the respective camshafts 120j by opening and closing of the pair of link members 215 as shown in FIG. 11 and FIG. 12, and, for example, in the opened state of the pair of link members 215 shown in FIG. 11, the respective eccentric cams 120i rotate clockwise with the respective camshafts 120j to be located in the first rotation position where the respective eccentric cams 120i are separated from the respective brake members 111. Namely, when the respective eccentric cams 120i are located in the first rotation position, the respective brake members 111 are also in the state separated from the respective exposed sites 40r, and therefore, the proximal end 40k sides of the inner guide sheaths 40 are movable forward and backward.

Further, in the closed state of the pair of link members 215 shown in FIG. 12, the respective eccentric cams 120i rotate counterclockwise with the respective camshafts 120j to contact the respective brake members 111. Thereby, the respective eccentric cams 120i rotate counterclockwise with the respective camshafts 120j to be located in the second rotation position where the respective eccentric cams 120i press the respective exposed sites 40r via the respective brake members 111 simultaneously in the vertical direction R to the wall surfaces 117w of the guide member 117 which the respective exposed sites 40r contact.

Note that in the second rotation position, contact points of the respective brake members 111 and the respective exposed sites 40r are points of action, the rotational centers of the respective camshafts 120j are fulcrums, the crossing position of the pair of link members 215 where the slider pin 130 is located is a power point, and by the lever force, the respective cam members 120 give pressing forces (braking forces) to the respective exposed sites 40r in the vertical direction R via the respective brake members 111. Thereby, forward and backward movement of the respective exposed sites 40r is simultaneously fixed.

Further, in the second rotation position, the respective brake members 111 crush contact sites to the exposed sites 40r which the respective brake members 111 contact in the vertical direction R.

Note that with opening and closing the pair of link members 215 having the same shapes, the respective eccentric cams 120i rotate between the second rotation position and the first rotation position in the same timing.

Next, an operation of the present embodiment will be described.

First, when the operator rotationally operates the fixing lever 80 clockwise, the reciprocating portion 110a of the crank member 110 moves forward in the operation portion 3. As a result, in the respective long holes 215h, the slider pin 130 moves forward, namely, to the distal end 215s sides of the pair of link members 215, whereby the crossing angle of the respective long holes 215h becomes large, and the crossing position of the pair of link members 215 moves to the distal end 215s sides. Thereby, as shown in FIG. 11, the respective eccentric cams 120i rotate clockwise to be located in the first rotation position with the respective camshafts 120j, and do not contact the brake members 111, and therefore, the respective eccentric cams 120i do not give braking forces to the exposed sites 40r of the inner guide sheaths 40.

Accordingly, as described above, when a rotation operation of the bending operation knob 9 is performed thereafter, the bending portion 7 bends from the proximal end of the second site 7b.

Next, when the operator rotationally operates the fixing lever 80 counterclockwise, the reciprocating portion 110a of the crank member 110 moves rearward in the operation portion 3. As a result, in the respective long holes 215h, the slider pin 130 moves rearward, namely, to the proximal end 215t sides of the pair of link members 215, whereby the crossing angle of the respective long holes 215h becomes smaller than that of FIG. 11, and the crossing position of the pair of link members 215 moves to the proximal end 215t sides. Thereby, as shown in FIG. 12, the respective eccentric cams 120i rotate counterclockwise to be located in the second rotation position with the respective camshafts 120j to contact the respective brake members 111.

Thereafter, the respective eccentric cams 120i press the respective exposed sites 40r in the vertical direction R to the wall surfaces 117w via the respective brake members 111, and therefore, the respective exposed sites 40r are sandwiched between the respective brake members 111 and the wall surfaces 117w to be fixed simultaneously. Note that in the second rotation position, the respective brake members 111 crush the contact sites to the exposed sites 40r which the respective brake members 111 contact in the vertical direction R.

Accordingly, as described above, when a rotational operation of the bending operation knob 9 is performed thereafter, the bending portion 7 bends from the proximal end of the first site 7a.

Note that in the second rotation position shown in FIG. 12, the slider pin 130 is fitted in the respective long holes 215h in the respective second parallel sites 215c, and the respective second parallel sites 215c are superimposed on each other in the direction Q. Thereby, the forces to open respectively are cancelled off in the respective second parallel sites 215c, and therefore, movement to the respective distal end 215s sides of the slider pin 130 in the respective long holes 215h is fixed.

As a result, the closed state of the pair of link members 215 is fixed, and therefore, the rotation position of the fixing lever 80 is fixed. Thereby, even if the surgeon takes his or her finger off from the fixing lever 80 in the second rotation position, fixation of the respective exposed sites 40r is not released.

Further, the respective long holes 215h are also folded at the boundaries of the respective connection sites 215b and the respective second parallel sites 215c. Thereby, when the slider pin 130 is fitted in the long holes 215h of the respective second parallel sites 215c from the long holes 215h of the respective connection sites 215b, click sensing occurs, and therefore, the surgeon can easily recognize fixation of the respective exposed sites 40r.

As above, in the present embodiment, it is shown that the eccentric cams 120i of the respective cam members 120 give the pressing forces in the vertical direction R to the respective exposed sites 40r via the respective brake members 111, and simultaneously fix the respective exposed sites 40r.

According thereto, when the eccentric cams 120i are directly pressed to the respective exposed sites 40r to fix the respective exposed sites 40r, as in the aforementioned first embodiment, strong braking forces can be obtained because contact areas of the eccentric cam 120i to the respective exposed sites 40r are small, and therefore, stress concentrates thereon, but when the outside diameters of the respective inner guide sheaths 40 are made small, and the material of the elemental wires of the coil pipes configuring the respective inner guide sheaths 40 is made soft, the eccentric cam 120i strongly crushes the respective exposed sites 40r, and a problem of inhibiting movement of the respective wires 30 that are inserted through the insides of the respective exposed sites 40r arises. Further if fixation of the respective exposed sites 40r is performed repeatedly, the respective exposed sites 40r are not restored and are plastically deformed to be in a crushed state, and that problems of inhibiting movement of the respective wires 30 inserted through the insides of the respective exposed sites 40r and inhibiting movement of the respective inner guide sheaths 40 in the respective outer guide sheaths 50 also arise.

However, in the configuration in which the respective brake members 111 contact the respective exposed sites 40r shown in the present embodiment, the pressing forces are dispersed because contact areas of the respective brake members 111 that give the pressing forces to the respective exposed sites 40r are larger than those of the respective eccentric cams 120i, and therefore, the pressing forces can be prevented from crushing the respective exposed sites 40r more than necessary.

Further, in the present embodiment, it is shown that the pair of link members 215 are each formed by being folded into the crank shapes.

According to the above, if the lengths in the axial direction of the respective link members 215 that cross each other are simply extended for the purpose of locating the power point of the lever away from the fulcrum in order to increase the braking force, the moving member fixing mechanism 100 becomes large. However, in the present embodiment, the respective link members 215 are folded into the crank shapes, whereby the power point is located away from the fulcrum, and therefore, the moving member fixing mechanism 100 does not become large in the insertion direction S and the vertical direction R. Accordingly, the moving member fixing mechanism 100 does not become large, and therefore, the moving member fixing mechanism 100 with a large braking force can be housed in the operation portion.

Furthermore, the pair of link members 215 have the lengths of the long holes 215h shorter than the pair of link members 115 of the first embodiment, and in addition, in the first rotation position, the slider pin 130 can be located close to the camshafts 120j of the cam members 120. Thereby, even with a small moving amount of the slider pin 130 in the insides of the long holes 215h, the cam members 120 can be rotated by a large amount, and therefore, the moving amount in the insertion direction S of the reciprocating portion 110a can be made small, and downsizing of the moving member fixing mechanism 100 can be realized. Further, the rotation amount of the fixing lever 80 also becomes small, and therefore, inhibition of the rotational operation of the bending operation knob 9 due to increase in the rotation amount of the fixing lever 80 is eliminated.

Further, in the present embodiment, it is shown that in the pair of link members 215, in the respective second parallel sites 215c, the long holes 215h are also formed along the respective second parallel sites 215c.

According to the above, in the configuration of the aforementioned first embodiment, when a surgeon takes his or her finger off from the fixing lever 80, the respective eccentric cams 120i rotate clockwise from the second rotation position shown in FIG. 12 by receiving the elastic restoring forces of the respective crushed exposed sites 40r to return to original states, and the pair of link members 115 are slightly opened, and slightly move to a front side of the reciprocating portion 110a, whereby the problem arises, that the fixing lever 80 rotates, and the braking force that fixes the respective exposed sites 40r becomes small. Therefore, the surgeon cannot take his or her finger off from the fixing lever 80.

Therefore, a lock mechanism that keeps the fixed state needs to be provided at another place not illustrated, and in addition, a click mechanism or the like for recognizing fixation needs to be additionally provided.

However, in the present embodiment, in the long holes 215h that are formed in the respective second parallel sites 215c, movement of the slider pin 130 can be fixed, and therefore, even if the surgeon takes his or her finger off from the fixing lever 80, the fixed state of the respective exposed sites 40r can be kept.

Accordingly, unlike the first embodiment, a lock mechanism does not have to be provided in another site, and the number of components can be reduced. In addition, when the surgeon performs the rotational operation of the fixing lever 80, the surgeon feels click sensing in his or her finger, and therefore can easily recognize fixation, so that the surgeon does not stop the fixing lever 80 halfway, and therefore, the effect of enabling a reliable switching operation is provided.

Note that the other effects are the same as those of the aforementioned first embodiment.

(Third Embodiment)

Figure 13:
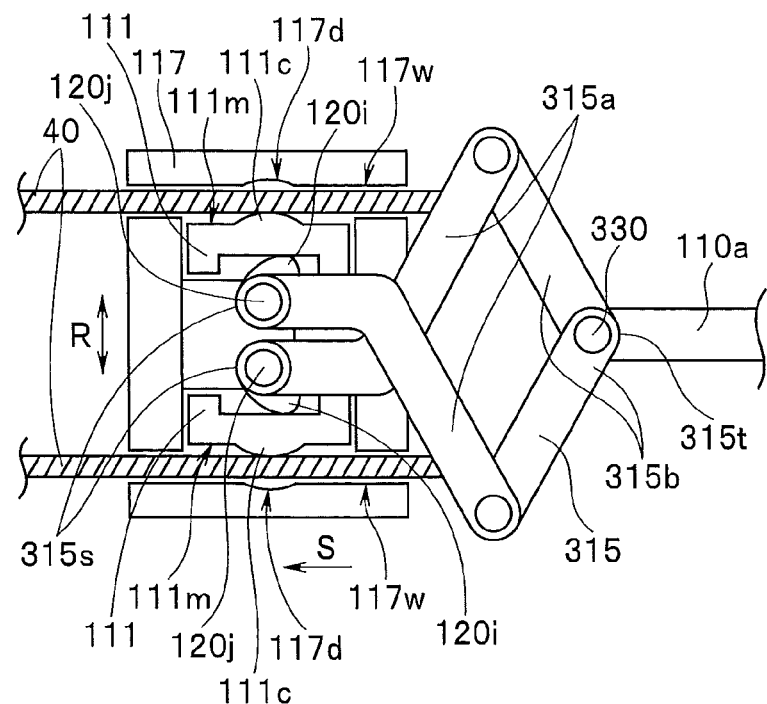
FIG. 13 is a view showing a third embodiment and schematically showing a state in which inner guide sheaths are unfixed by a moving member fixing mechanism provided in an operation portion of an endoscope.
Figure 14:
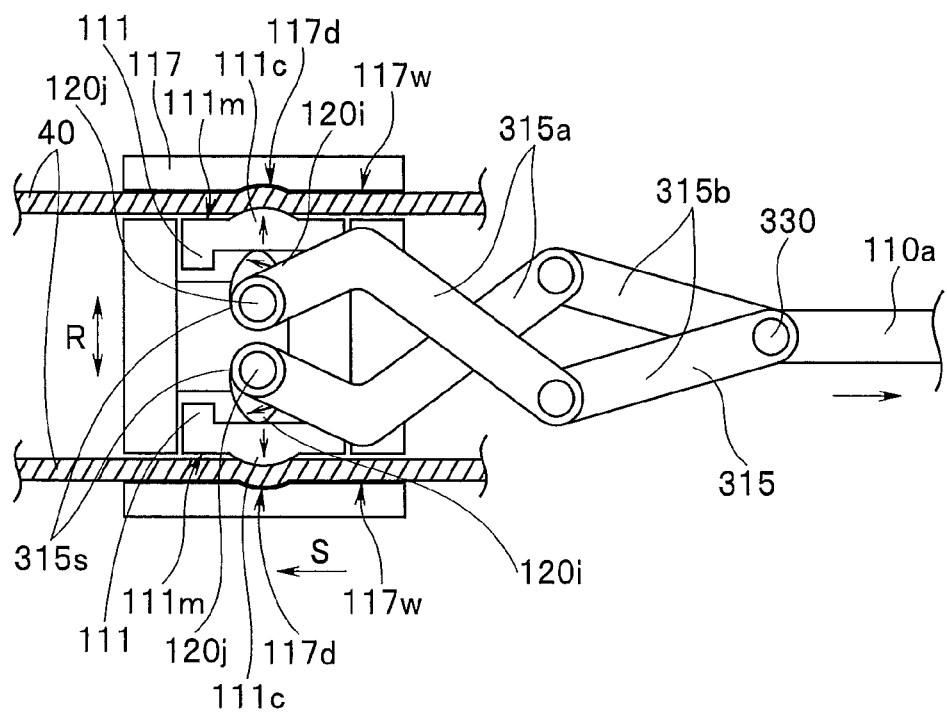
FIG. 14 is a view schematically showing a state in which the inner guide sheaths are fixed by the moving member fixing mechanism of FIG. 13.
Figure 15:
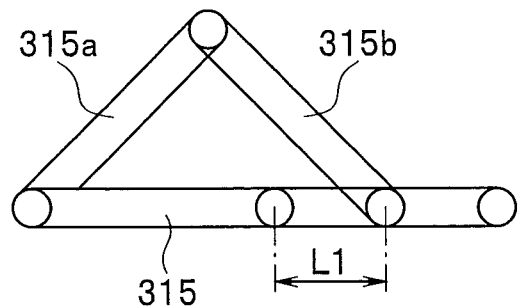
FIG. 15 is a view showing a state in which a first link and a second link are formed to have same lengths, in a pair of link members of FIG. 13 and FIG. 14.
Figure 16:
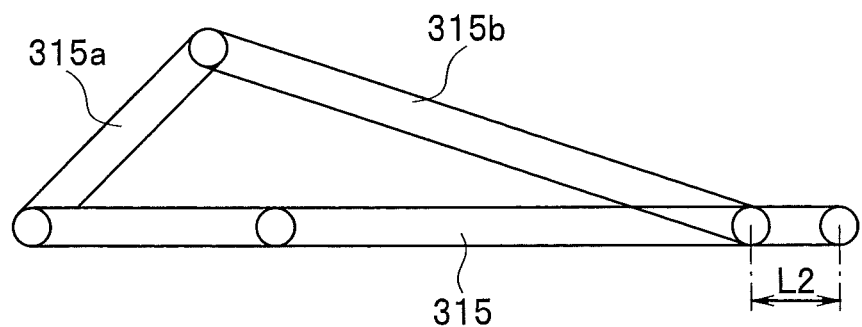
FIG. 16 is a view schematically showing a state in which the second link is formed to be longer than the first link, in the pair of link members of FIG. 13 and FIG. 14.

FIG. 13 is a view showing a third embodiment and schematically showing a state in which inner guide sheaths are unfixed by a moving member fixing mechanism provided in an operation portion of an endoscope. FIG. 14 is a view schematically showing a state in which the inner guide sheaths are fixed by the moving member fixing mechanism of FIG. 13. FIG. 15 is a view schematically showing a state in which a first link and a second link are formed to have same lengths in a pair of link members of FIG. 13 and FIG. 14. FIG. 16 is a view schematically showing a state in which the second link is formed to be longer than the first link, in the pair of link members of FIG. 13 and FIG. 14.

As compared with the endoscope of the second embodiment shown in FIG. 10 to FIG. 12 described above, a configuration of the endoscope of the third embodiment differs in the point in which convex portions are provided on surfaces facing exposed sites of inner guide sheaths, of brake members, the point in which concave portions are provided at positions facing the convex portions, in wall surfaces of a guide member, and the point in which the pair of link members are configured by quadric links.

Accordingly, only the differences will be described, the similar components to those in the second embodiment will be assigned with the same reference signs, and explanation thereof will be omitted. Note that in FIG. 13 and FIG. 14, the crank member 110 is shown by the other portions than the reciprocating portion 110a being omitted.

In the present embodiment, as shown in FIGS. 13 and 14, convex portions 111c with contact surfaces having partial circular-arc shapes are formed in substantial centers in the insertion direction S of surfaces facing the respective exposed sites 40r of the respective brake members 111, namely, surfaces 111m that contact the respective exposed sites 40r.

Further, in the wall surfaces 117w of the guide member 117, at sites facing the respective convex portions 111c, concave portions 117d in partial circular-arc shapes having the same radiuses of curvature as the respective convex portions 111c are respectively formed.

Note that contrary to FIG. 13 and FIG. 14, the convex portion may be formed on the wall surface 117w, while the concave portion may be formed on the surface 111m, and the curvatures of the convex portion 111c and the concave portion 117d may differ from each other.

Further, a pair of link members 315 that rotate the respective cam members 120 are each configured by a first link 315a that is located at a front half portion, and has a distal end side having a shape folded to be located parallel with the insertion direction S in the first rotation position, and a second link 315b that is rotatably connected to a proximal end of the first link 315a and has a linear shape. Further, the pair of link members 315 cross each other in distal end 315s sides of the first links 315a that are one ends, and proximal ends 315t of the second links 315b, that are the other ends, and are rotatably connected to a distal end of the reciprocating portion 110a with a pin 330 fitted in a crossing position of the proximal ends 315t. Namely, the pair of link members 315 are configured by known quadric links.

Note that the respective cam members 120 are rotatably connected to the distal ends 315s of the pair of link members 315.

The pair of link members 315 are configured to be openable and closable to an opened state as shown in FIG. 13 and a closed state shown in FIG. 14 by forward and rearward movement of the crossing sites by forward and rearward movement of the pin 330 accompanying forward and rearward movement of the reciprocating portion 110a.

The respective eccentric cams 120i rotate with the respective camshafts 120j by opening and closing of the pair of link members 315 as shown in FIG. 13 and FIG. 14, and, for example, in the opened state of the pair of link members 315 shown in FIG. 13, the respective eccentric cams 120i rotate clockwise with the respective camshafts 120j to be located in the first rotation position where the respective eccentric cams 120i are separated from the respective brake members 111.

Namely, when the respective eccentric cams 120i are located in the first rotation position, the respective brake members 111 are also in a state kept separated from the respective exposed sites 40r, and therefore, the proximal end 40k sides of the respective inner guide sheaths 40 are movable forward and rearward.

Further, in the closed state of the pair of link members 315 shown in FIG. 14, the respective eccentric cams 120i rotate counterclockwise with the respective camshafts 120j to contact the respective brake members 111. Thereby, the respective eccentric cams 120i rotate counterclockwise with the respective camshafts 120j to be located in the second rotation position where the respective eccentric cams 120i simultaneously press the respective exposed sites 40r via the respective brake members 111 in the vertical direction R to the wall surfaces 117w of the guide member 117 which the respective exposed sites 40r contact.

Note that as shown in FIG. 14, in the second rotation position, the respective exposed sites 40r are brought into a state in which the respective exposed sites 40r are deformed and crushed, namely, folded by being sandwiched between the convex portions 111c of the respective brake members 111 and the concave portions 117d of the guide member 117. Thereby, movement of the respective exposed sites 40r is fixed.

Further, the curvatures of the convex portions 111c and the concave portions 117d, and the moving amounts in the vertical direction R of the respective brake members 111 are specified so that the respective exposed sites 40r are deformed to such an extent that the insertion resistances of the respective wires 30 that are inserted through the insides of the respective exposed sites 40r do not increase, in the second rotation position.

As above, in the present embodiment, it is shown that the convex portions 111c are formed on the facing surfaces 111m to the respective exposed sites 40r of the respective brake members 111, and the concave portions 117d are formed at the facing sites to the convex portions 111c, of the wall surfaces 117w of the guide member 117.

According to the above, as compared with fixing the respective exposed sites 40r with the linear shapes of the respective exposed sites 40r being kept by sandwiching the respective exposed sites 40r in the vertical direction R by using the brake members 111 the facing surfaces 111m of which are configured by the flat surfaces as in the first and the second embodiments described above, the configuration that fixes the respective exposed sites 40r by partially deforming the respective exposed sites 40r by using the convex portions 111c and the concave portions 117d is included, and therefore, the fixing forces can be enhanced because the respective inner guide sheaths 40 do not easily slide forward and rearward when the bending forces are applied to the respective inner guide sheaths 40 by the respective wires 30.

Accordingly, even if the crushing amounts of the respective exposed sites 40r are reduced compared with the case in the first and the second embodiments, the fixing forces can be enhanced, and therefore, the working force that rotates the fixing lever 80 at the time of fixing can be reduced.

Further, in the present embodiment, it is shown that the pair of link members 315 are configured by quadric links.

According to the above, unlike the first and the second embodiments described above, a force can be applied to the distal end 315s of the first link 315a from beginning of movement of the reciprocating portion 110a, and therefore, the operation force amount of the fixing lever 80 can be reduced.

Further, as shown in FIG. 15, the first link 315a and the second link 315b are not formed to have the same lengths (315a=315b), but the length of the second link 315b is made longer than that of the first link 315a (315a<315b), whereby a moving amount in the insertion direction S of the reciprocating portion 110a which is necessary for rotating the eccentric cam 120i by the same rotation angle can be made small (L1>L2). Thereby, the rotation amount of the fixing lever 80 can be made small, and therefore, inhibition of the rotational operation of the bending operation knob 9 as a result of the rotation amount of the fixing lever 80 being increased is eliminated.

Note that the other effects are the same as those of the second embodiment described above.

Figure 17:
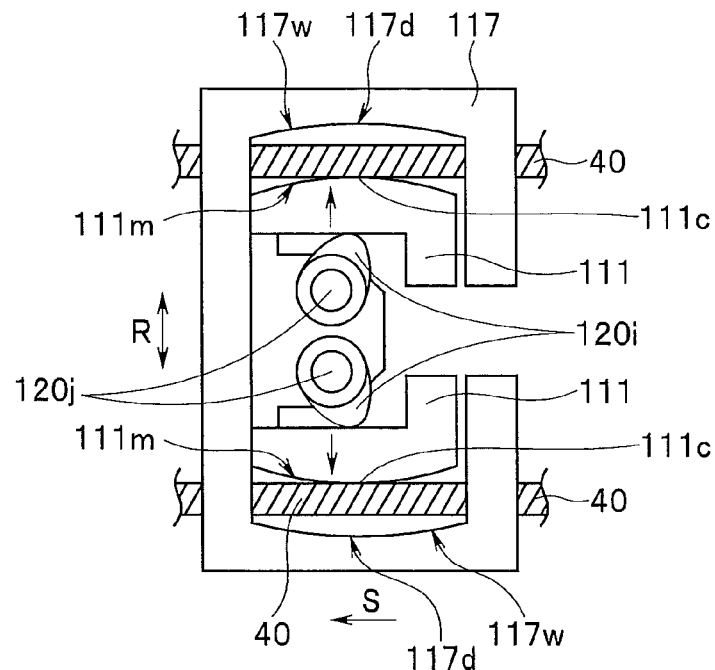
FIG. 17 is a view showing a modification in which curvatures of convex portions of brake members and concave portions of wall surfaces are made larger than those of FIG. 13 and FIG. 14.
Figure 18:
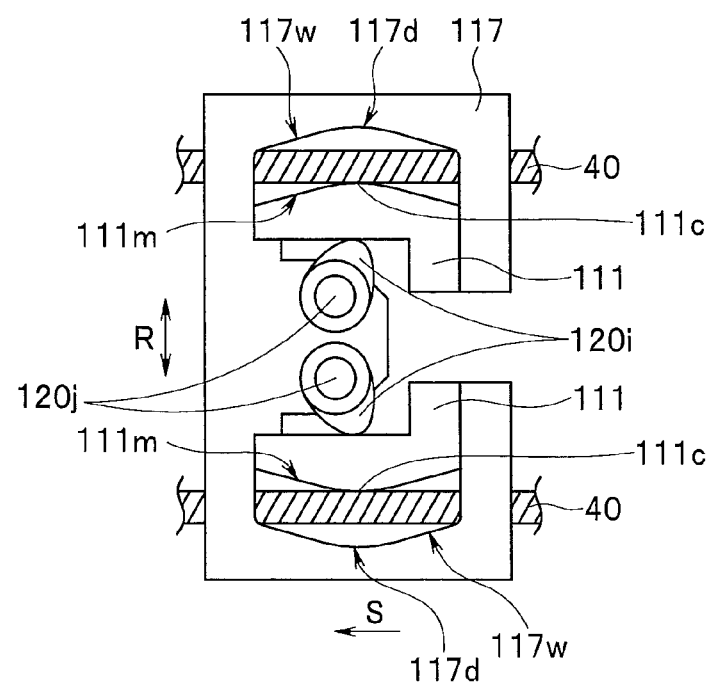
FIG. 18 is a view showing a modification in which curvatures of convex portions of brake members and concave portions of wall surfaces are made larger than those of FIG. 17.

Further, hereinafter, a modification will be shown with use of FIG. 17 and FIG. 18. FIG. 17 is a view showing a modification in which curvatures of convex portions of brake members and concave portions of wall surfaces are made larger than those of FIG. 13 and FIG. 14. FIG. 18 is a view showing a modification in which curvatures of convex portions of brake members and concave portions of wall surfaces are made larger than those of FIG. 17.

As shown in FIG. 17, the convex portions 111c that are formed on the facing surfaces 111m to the respective exposed sites 40r, of the respective brake members 111, and the concave portions 117d that are formed on the wall surfaces 117w of the guide member 117 may be formed to have curvatures larger than those of the convex portions 111c and the concave portions 117d shown in FIG. 13 and FIG. 14, for example, R=40 to 60.

According to the above, in the configuration shown in FIG. 13 and FIG. 14, the curvatures of the convex portions 111c and the concave portions 117d are small, and therefore, the braking forces that are given to the respective exposed sites 40r from the respective brake members 111 concentrate on the convex portions 111c, whereby the problem arises, that the deformation amounts of the respective exposed sites 40r become large, and movement of the wires 30 that are inserted through the insides of the respective exposed sites 40r is inhibited. However, if the curvatures of the convex portions 111c and the concave portions 117d are made large as shown in FIG. 17, the respective exposed sites 40r can be deformed with large contact areas, and therefore, the aforementioned problem can be solved. Note that the other effects are the same as those of the present embodiment.

Further, if the curvatures of the convex portions 111c and the concave portions 117d are made larger as shown in FIG. 18 than the curvatures shown in FIG. 17, the similar effect to that of FIG. 17 can be obtained.

(Fourth Embodiment)

Figure 19:
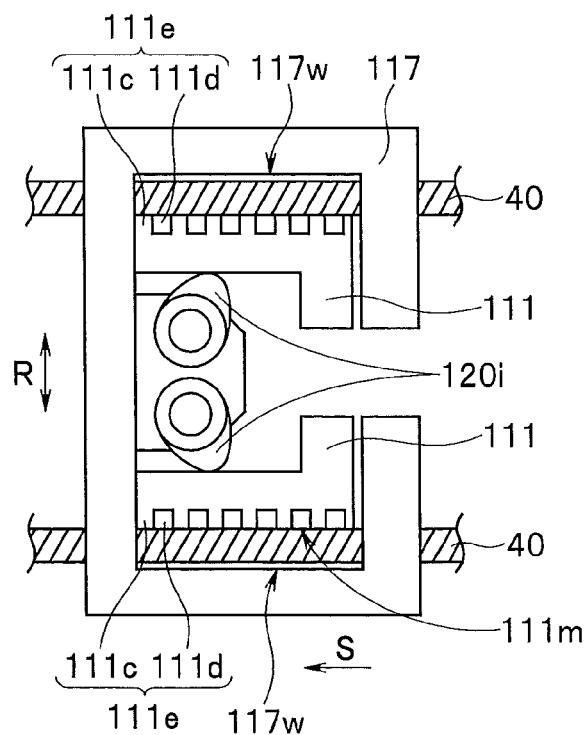
FIG. 19 is a view showing a configuration in which a plurality of convex and concave portions are formed along an insertion direction on surfaces facing exposed sites, of brake members in a moving member fixing mechanism provided in an operation portion of an endoscope of a fourth embodiment.
Figure 20:
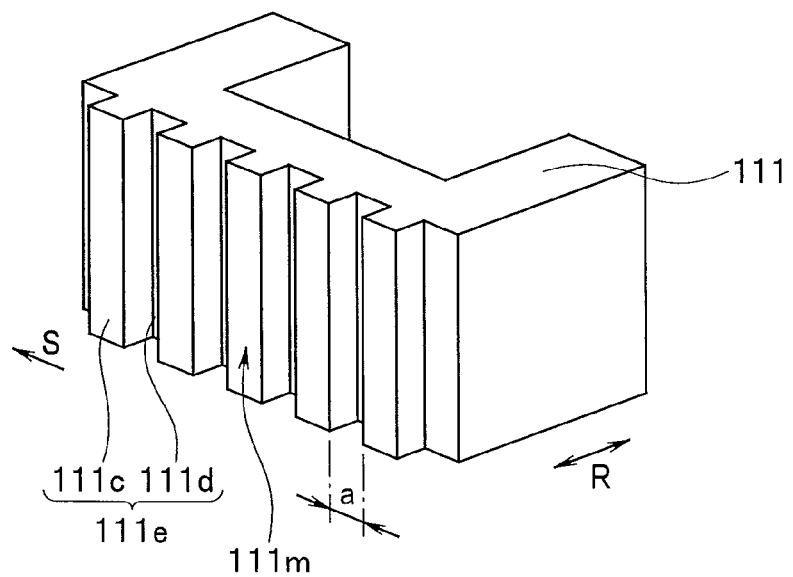
FIG. 20 is a perspective view showing the brake member of FIG. 19 under enlargement.
Figure 21:
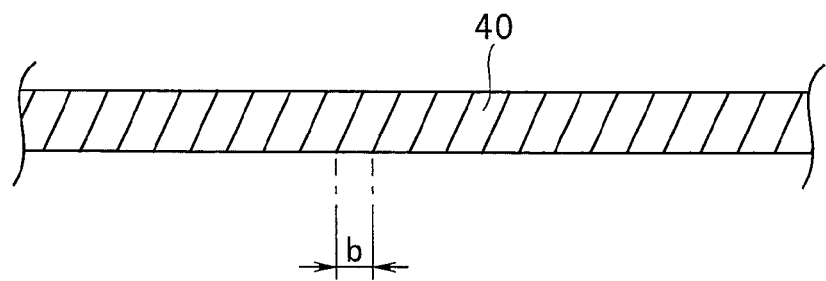
FIG. 21 is a view showing an inner guide sheath of FIG. 19 under enlargement.

FIG. 19 is a view showing a configuration in which a plurality of convex and concave portions are formed along an insertion direction on surfaces facing exposed sites, of brake members, in a moving member fixing mechanism provided in an operation portion of an endoscope of the present embodiment. FIG. 20 is a perspective view showing the brake member of FIG. 19 under enlargement. FIG. 21 is a view showing an inner guide sheath of FIG. 19 under enlargement.

A configuration of the endoscope of the fourth embodiment differs in the point that the concave and convex portions are provided on the surfaces that contact the exposed sites of the respective inner guide sheaths, of the respective brake members, as compared with the endoscope of the second embodiment shown in FIG. 10 to FIG. 12 described above.

Accordingly, only the difference will be described, the similar components to those in the first to the third embodiments will be assigned with the same reference signs, and explanation thereof will be omitted. Note that in FIG. 19, the configuration is shown with the crank member being omitted.

As shown in FIG. 19 and FIG. 20, in the present embodiment, convex portions 111c and concave portions 111d are alternately formed along the insertion direction S, on the surfaces 111m facing the exposed sites 40r, of the respective brake members 111, and thereby, a plurality of concave and convex portions 111e are formed along the insertion direction S, on the surfaces 111m.

Note that as shown in FIG. 20, a width a of the concave portion 111d in the insertion direction S is formed to be larger than an elemental wire width b of each of the coil pipes that configure the respective exposed sites 40r (a>b). This is for a part of the elemental wire of the coil to be fitted in the concave portion 111d when the concave and convex portions 111e contact the respective exposed sites 40r in the second rotation position that fixes movement of the respective exposed sites 40r. Namely, the concave portion 111d has the width in which a part of the elemental wire is always fitted in the insertion direction S.

According the above configuration, when the concave and convex portions 111e contact the respective exposed sites 40r in the second rotation position, the contact areas of the respective brake members 111 are decreased to be smaller than those in the second embodiment. However, since the elemental wires of the coil are fitted in a plurality of the concave portions 111d, frictional resistances to the respective exposed sites 40r can be made larger than those in the second embodiment, and therefore, braking forces that are given to the respective exposed sites 40r can be made large.

Figure 23:
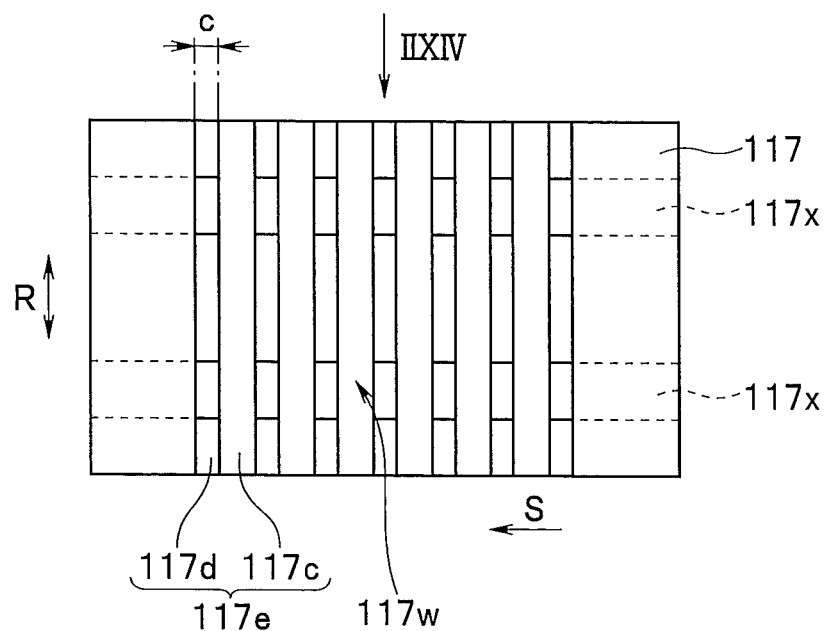
FIG. 23 is a view showing a modification in which a plurality of concave and convex portions are also formed along an insertion direction on the wall surface of the guide member of FIG. 19.

Note that the other effects are the same as those in the second embodiment described above. Further, as shown in FIG. 23, a width c of the concave portion 117d in the insertion direction S may be formed to be larger than the elemental wire width b of the coil pipes configuring the respective exposed sites 40r (c>b).

Figure 22:
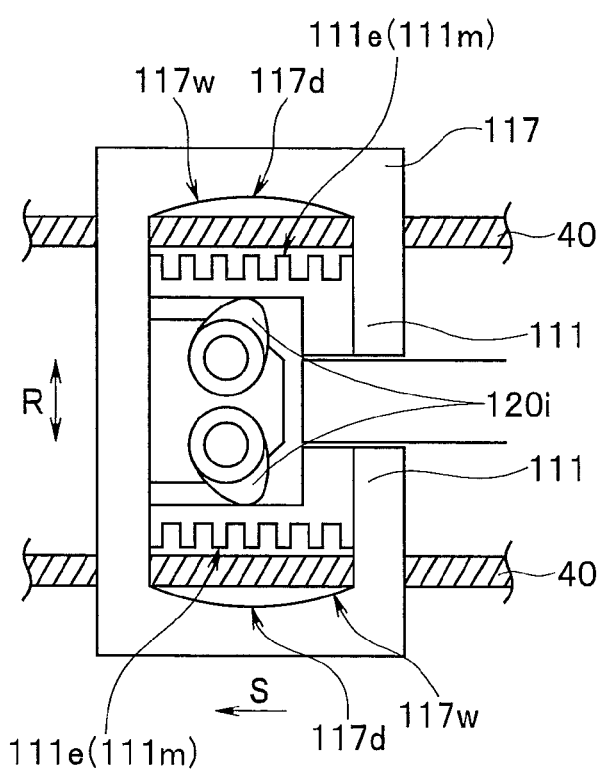
FIG. 22 is a view showing a modification in which concave portions with large curvatures are provided on wall surfaces of a guide member of FIG. 19.

Further, hereinafter, a modification will be shown with use of FIG. 22. FIG. 22 is a view showing the modification in which concave portions with large curvatures are provided on wall surfaces of a guide member of FIG. 19.

As shown in FIG. 22, in a state in which the aforementioned concave and convex portions 111e are formed on the facing surfaces 111m of the brake members 111, the concave portions 117d with large curvatures as shown in FIG. 17 described above may be formed on the wall surfaces 117w of the guide member 117. Note that in the concave portion 117d, a plurality of concave and convex portions may be further formed.

Figure 24:
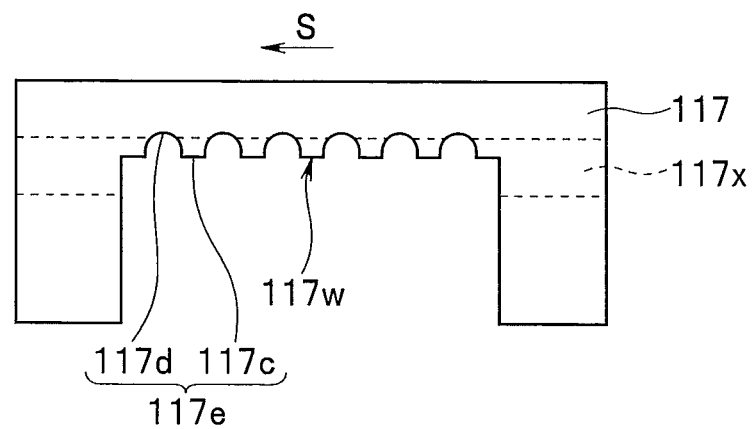
FIG. 24 is a view of the guide member of FIG. 23 seen from the IIXIV direction in FIG. 23.

Furthermore, hereinafter, a modification will be shown with use of FIG. 23 and FIG. 24. FIG. 23 is a view showing the modification in which a plurality of concave and convex portions are also formed along the insertion direction on the wall surfaces of the guide member of FIG. 19. FIG. 24 is a view of the guide member of FIG. 23 seen from the IIXIV direction in FIG. 23.

As shown in FIG. 23 and FIG. 24, on the wall surfaces 117w of the guide member 117, convex portions 117c and the concave portions 117d are also alternately formed along the insertion direction S, whereby a plurality of concave and convex portions 117e may be formed along the insertion direction S, on the wall surface 117w.

Figure 25:
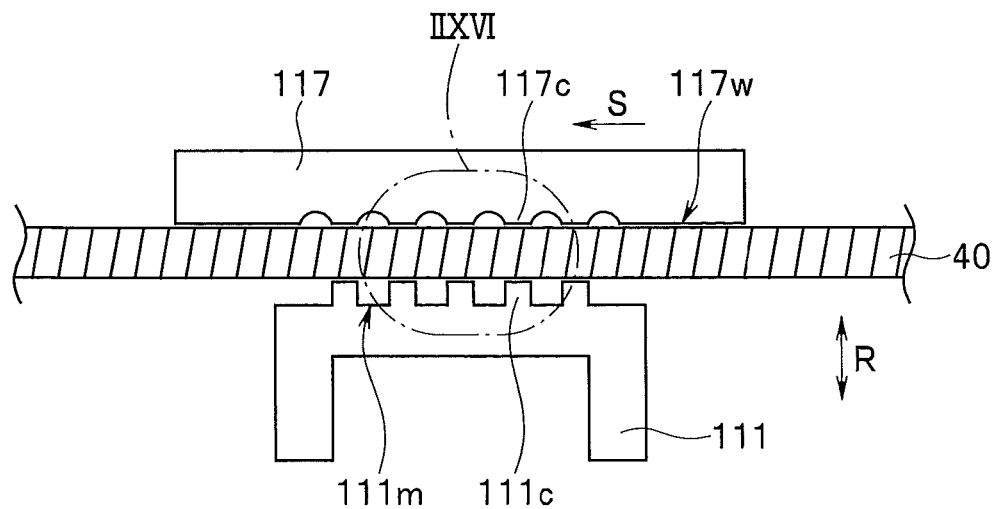
FIG. 25 is a view showing a modification in which concave and convex portions are formed on both a facing surface to an exposed site of the inner guide sheath, of the brake member of FIG. 11, and the wall surface of the guide member.
Figure 26:
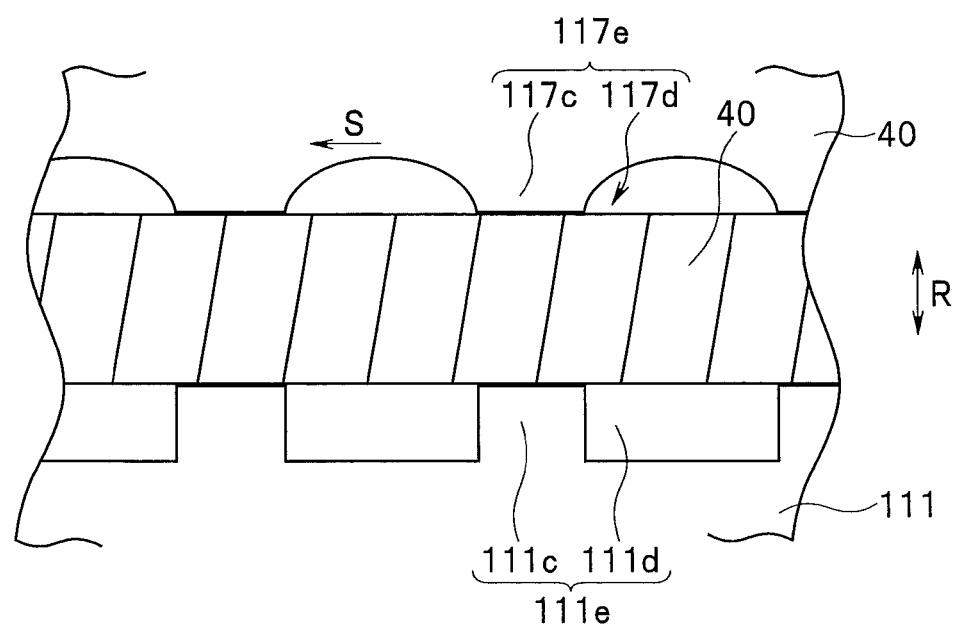
FIG. 26 is a view showing a site enclosed by the IIXVI in FIG. 25 under enlargement.

Further, hereinafter, a modification will be shown with use of FIG. 25 and FIG. 26. FIG. 25 is a view showing the modification in which concave and convex portions are formed on both of the facing surfaces to the exposed sites of the inner guide sheaths, of the brake members, and the wall surfaces of the guide member of FIG. 11. FIG. 26 is a view showing a site enclosed by IIXVI in FIG. 25 under enlargement.

As shown in FIG. 25 and FIG. 26, on the surfaces 111m facing the respective exposed sites 40r, of the respective brake members 111, the convex portions 111c and the concave portions 111d are alternately formed along the insertion direction S. As a result, a plurality of the concave and convex portions 111e are formed along the insertion direction S, on the surface 111m, and the convex portions 117c and the concave portions 117d are also alternately formed along the insertion direction S, on the wall surface 117w of the guide member 117. Thereby, a plurality of concave and convex portions 117e may be formed along the insertion direction S, on the wall surface 117w.

Note that as shown in FIG. 26, the convex portions 111c of the brake member 111 are located to face the convex portions 117c of the guide member 117, and the concave portions 111d are located to face the concave portions 117d.

Further, in the second rotation position that fixes movement of the respective exposed sites 40r, the respective exposed sites 40r are deformed in the vertical direction R by being sandwiched in the vertical direction R by the convex portions 111c and the convex portions 117c, and thereby movement is fixed.

Note that in the fixed state, the respective exposed sites 40*r* that are located between the concave portions 111*d* and the convex portions 117*c* are in a non-deformed state.

This is because when the respective exposed sites 40*r* displace forward and rearward in the fixed state, the non-deformed sites of the respective exposed sites 40*r* abut on the convex portions 111*c* or the convex portions 117*c*, and therefore, the positions of the respective exposed sites are restrained so that the respective exposed sites 40*r* do not displace forward and rearward any more.

Figure 27:
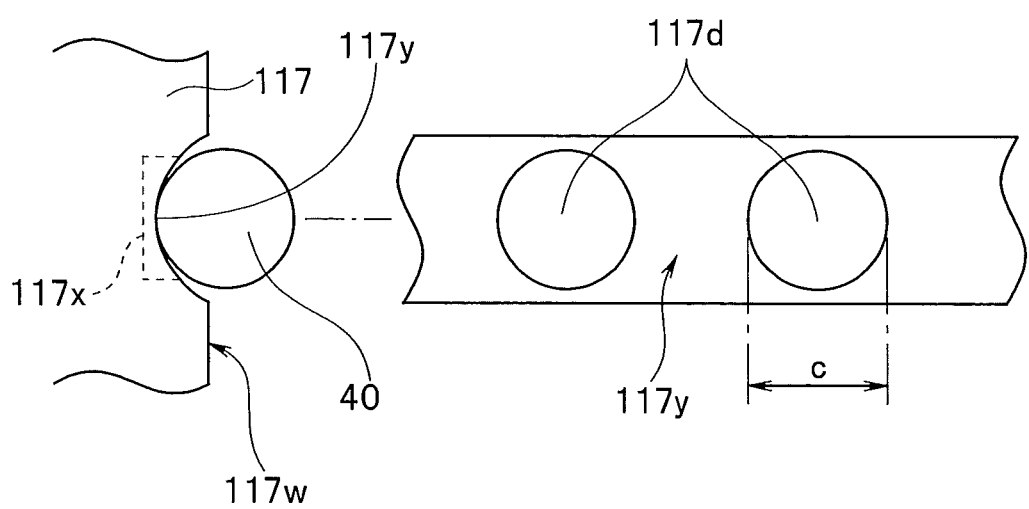
FIG. 27 is a view showing a modification in which a concave portion is formed in guide grooves for the respective inner guide sheaths formed on the wall surface of the guide member of FIG. 11.

Furthermore, hereinafter, a modification will be shown with use of FIG. 27. FIG. 27 is a view showing the modification in which a concave portion is formed in the guide groove for the respective inner guide sheaths, which is formed on the wall surface of the guide member of FIG. 11.

As shown in FIG. 27, at least one circular concave portion 117*d* having a diameter c may be formed on a surface facing the respective inner guide sheaths 40 in each of guide grooves 117*y* in partial circular-arc shapes for the respective inner guide sheaths 40, which are formed on the wall surfaces 117*w* of the respective guide members 117.

Note that the diameter c is formed to be larger than the elemental wire width b of the coil pipes configuring the respective exposed sites 40*r* (c>b).

(Fifth Embodiment)

Figure 28:
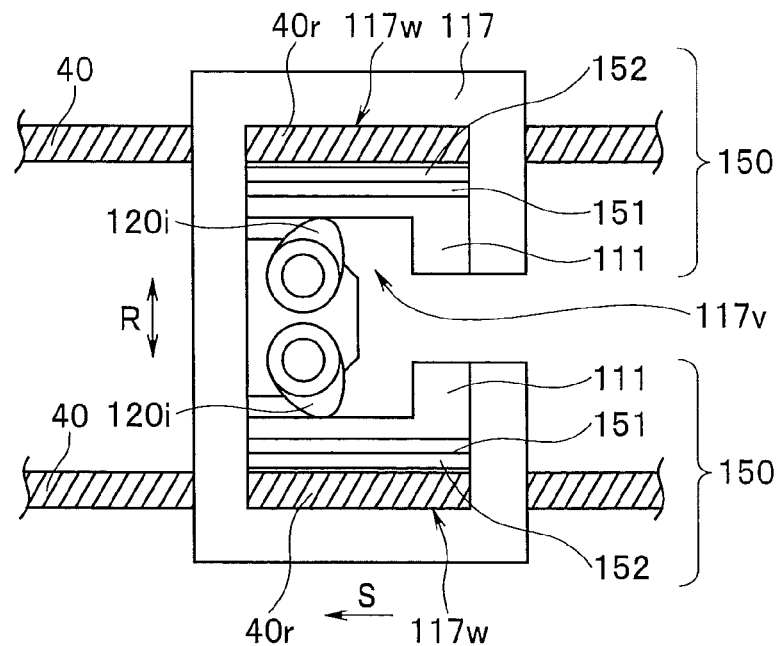
FIG. 28 is a view showing a fifth embodiment, and schematically showing a state in which inner guide sheaths are unfixed by a moving member fixing mechanism provided in an operation portion of an endoscope.

FIG. 28 is a view showing the present embodiment and schematically showing a state in which inner guide sheaths are unfixed by a moving member fixing mechanism provided in an operation portion of an endoscope.

A configuration of the endoscope of the fifth embodiment differs in the point in which in a space in a guide member, interposition members that are interposed between cam members and respective exposed sites are each configured by having a brake member, a deformation member and a contact member, as compared with the endoscope of the second embodiment shown in FIG. 10 to FIG. 12, the endoscope of the third embodiment shown in FIG. 13 to FIG. 16, and the endoscope of the fourth embodiment shown in FIG. 19 to FIG. 21 that are described above.

Accordingly, only the difference will be described, the similar components to those in the second to the fourth embodiments will be assigned with the same reference signs, and explanation thereof will be omitted. Note that in FIG. 28, the configuration is shown with the crank member 110 being omitted.

As shown in FIG. 28, in the space 117*v* in the guide member 117, a pair of interposition members 150 that are provided in positions sandwiched by the eccentric cams 120*i* of the cam members 120 and the respective exposed sites 40*r* in the vertical direction R are configured by the pair of brake members 111 that are pressing members, a pair of deformation members 151, and a pair of contact members 152 in the present embodiment.

As described above, the respective brake members 111 are members which the respective eccentric cams 120*i* contact in the second rotation position that fixes movement of the respective exposed sites 40*r*, and the respective eccentric cams 120*i* press to an outer side in the vertical direction R.

The respective deformation members 151 are members that are located between the respective brake members 111 and the respective exposed sites 40*r* in the vertical direction R, and deform in the vertical direction R with pressing forces from the respective eccentric cams 120*i* to the respective brake members 111 in a state in which the respective contact members 152 contact the respective exposed sites 40*r* in the second rotation position.

Note that the respective deformation members 151 are configured by a shape memory alloy (Ni—Ti alloy) or the like that is a material more easily deformable than the stainless steel that configures the coil sheaths of the respective inner guide sheaths 40.

The respective contact members 152 are plate-shaped members that are located between the respective deformation members 151 and the respective exposed sites 40*r* in the vertical direction R, press the respective exposed sites 40*r* in the second rotation position, and stop movement in the insertion direction S of the respective exposed sites 40*r* with frictional forces.

Note that the respective contact members 152 are configured by the same material as that of the respective inner guide sheaths 40. Namely, the respective contact members 152 are configured by plate-shaped members of stainless steel.

Further, the reason why in the vertical direction R, the respective contact members 152 are sandwiched between the respective deformation members 151 and the respective exposed sites 40*r*, namely, the reason why the respective deformation members 151 are not brought into direct contact with the respective exposed sites 40*r* is that if the respective deformation members 151 are brought into direct contact with the respective exposed sites 40*r* configured by stainless steel, the respective deformation members 151 that are configured by a different material from the respective exposed sites 40*r* are worn out.

Next, an operation of the present embodiment will be described.

When the respective eccentric cams 120*i* rotate, and press the respective brake members 111 to the respective exposed site 40*r* sides in the vertical direction R, in the second rotation position, the respective contact members 152 press the respective exposed sites 40*r*.

Thereby, movement in the insertion direction S of the respective exposed sites 40*r* is fixed, and at this time, the respective deformation members 151 sandwiched between the respective contact members 152 and the respective brake members 111 are very slightly crushed in the vertical direction R and deformed. Note that the shapes of the respective deformation members 151 return to the shapes before the respective deformation members 151 are crushed when fixation of the respective exposed sites 40*r* is released.

According to the configuration as above, in the second rotation position, the respective deformation members 151 can absorb variations within permissible dimensional deviation of the respective eccentric cams 120*i*, the respective brake members 111, the guide member 117, the respective inner guide sheaths 40, the pair of link members (115, 215, 315, and the like) that are used in fixing the movement of the respective exposed sites 40*r*. Therefore, simultaneous fixation of the four exposed sites 40*r* is easily performed, and therefore, the rotational force amount of the fixing lever 80 can be reduced.

Namely, if the deformation members 151 are not included, the fixing force is further increased until the last exposed site 40*r* is fixed after one of the exposed sites 40*r* is fixed first among the four exposed sites 40*r* according to the combination of the dimensions of the related components, though the exposed site 40*r* that is fixed first to the third exposed site 40*r* are already fixed sufficiently, and therefore, a force more than necessary is required.

However, since the deformation member 151 is configured to be deformed for the first time with the force slightly exceeding the force necessary for fixation by the thickness and material quality thereof, a force more than necessary does not have to be used to fix the four exposed sites 40*r*, and the rotational force amount of the fixing lever 80 can be reduced.

Note that other effects are the same as those in the second to the fourth embodiments described above.

Further, in the present embodiment, it is shown that the respective deformation members 151 are configured by a shape memory alloy (Ni—Ti alloy). The respective deformation members 151 are not limited thereto, and may be configured by any material such as a rigid polymeric material, and a spring material if only it is the material that deforms for the first time with a force slightly exceeding a necessary fixing force, and restores from deformation when the force is released.

(Sixth Embodiment)

Figure 29:
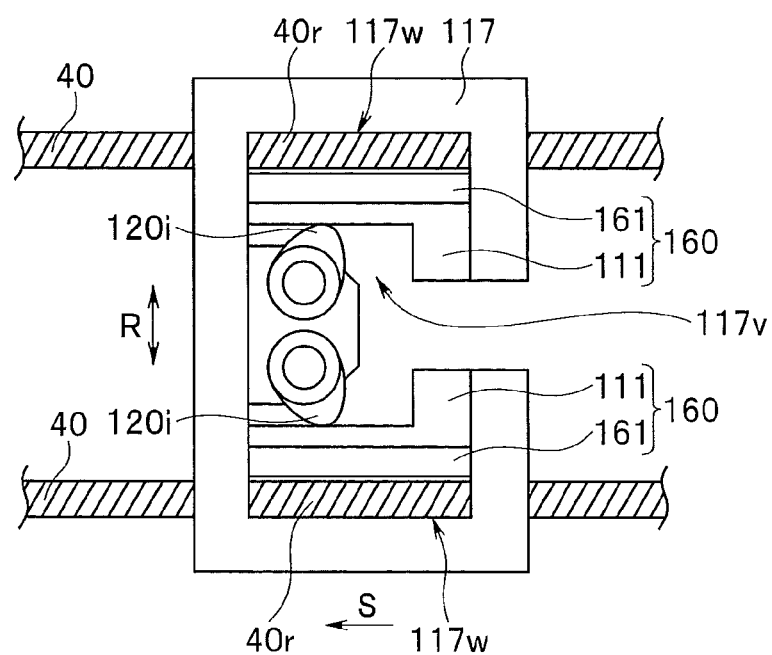
FIG. 29 is a view showing a sixth embodiment, and schematically showing a state in which inner guide sheaths are unfixed by a moving member fixing mechanism provided in an operation portion of an endoscope.

FIG. 29 is a view showing the present embodiment and schematically showing a state in which inner guide sheaths are unfixed by a moving member fixing mechanism provided in an operation portion of an endoscope.

A configuration of the endoscope of the sixth embodiment differs in the point in which in a space in a guide member, interposition members interposed between respective cam members and respective exposed sites are each configured by a brake member, and a frictional engagement member, as compared with the endoscope of the second embodiment shown in FIG. 10 to FIG. 12, the endoscope of the third embodiment shown in FIG. 13 to FIG. 16, and the endoscope of the fourth embodiment shown in FIG. 19 to FIG. 21 that are described above.

Accordingly, only the difference will be described, the similar components to those in the second to the fourth embodiments will be assigned with the same reference signs, and explanation thereof will be omitted. Note that in FIG. 29, the configuration is shown with the crank member 110 being omitted.

As shown in FIG. 29, in the space 117*v* in the guide member 117, interposition members 160 that are provided in positions sandwiched by the eccentric cams 120*i* of the respective cam members 120 and the respective exposed sites 40*r* in the vertical direction R are configured by the pair of brake members 111 that are pressing members, and a pair of frictional engagement members 161 in the present embodiment.

As described above, the respective brake members 111 are members which the respective eccentric cams 120*i* contact in the second rotation position that fixes movement of the respective exposed sites 40*r*, and the respective eccentric cams 120*i* press to an outer side in the vertical direction R.

The respective frictional engagement members 161 are members that are located between the respective brake members 111 and the respective exposed sites 40*r* in the vertical direction R, and press the respective exposed sites 40*r* in the vertical direction R in the second rotation position, and stop the movement in the insertion direction S of the respective exposed sites 40*r* with frictional forces.

Note that the respective frictional engagement members 161 are configured by, so-called brake pads for a motorcycle and an automobile, which are formed by mixing potassium titanate whiskers being into a phenol resin and solidifying the mixture.

According to the configuration as above, the respective frictional engagement members 161 that gives fixing forces to the respective exposed sites 40*r* in the second rotation position are configured by the material excellent in braking force, and therefore, are not easily worn out, and even if the frictional engagement members 161 are somewhat worn, the frictional engagement members 161 can keep sufficient braking forces.

Note that the other effects are the same as those in the second to the fourth embodiments described above.

(Seventh Embodiment)

Figure 30:
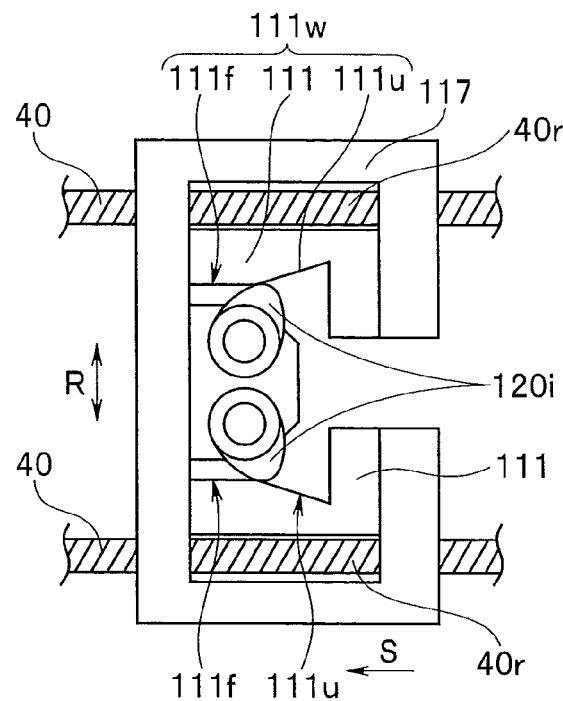
FIG. 30 is a view showing a seventh embodiment and schematically showing a state in which inner guide sheaths are unfixed by a moving member fixing mechanism provided in an operation portion of an endoscope.
Figure 31:
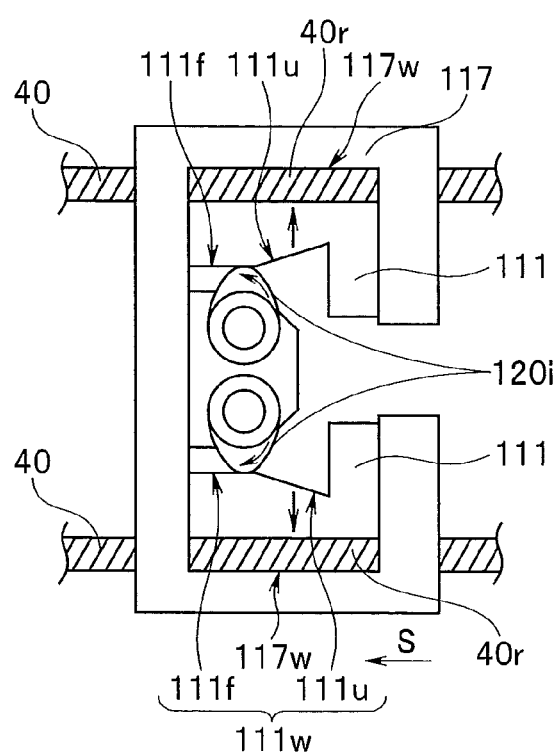
FIG. 31 is a view schematically showing a state in which the inner guide sheaths are fixed by the moving member fixing mechanism of FIG. 30.

FIG. 30 is a view showing the present embodiment and schematically showing a state in which inner guide sheaths are unfixed by a moving member fixing mechanism provided in an operation portion of an endoscope. FIG. 31 is a view schematically showing a state in which the inner guide sheaths are fixed by the moving member fixing mechanism of FIG. 30.

A configuration of the endoscope of the seventh embodiment differs in the point in which an inclined surface is formed on a surface, which an eccentric cam contacts, of a brake member in the first rotation position, as compared with the endoscope of the second embodiment shown in FIG. 10 to FIG. 12, the endoscope of the third embodiment shown in FIG. 13 to FIG. 16, the endoscope of the fourth embodiment shown in FIG. 19 to FIG. 21, the endoscope of the fifth embodiment shown in FIG. 28, and the endoscope of the sixth embodiment shown in FIG. 29 that are described above.

Accordingly, only the difference will be described, the similar components to those in the second to the sixth embodiments will be assigned with the same reference signs, and explanation thereof will be omitted. Note that in FIG. 30 and FIG. 31, the configuration is shown with the crank member 110 omitted.

As shown in FIG. 30 and FIG. 31, on at least parts of the surfaces 111*w*, which the respective eccentric cams 120*i* contact, of the respective brake members 111, more specifically, on the surfaces 111*w* which the respective eccentric cams contact in the first rotation position, linear inclined surfaces 111*u* that incline to extend toward an inner side in the vertical direction R as the inclined surfaces extend to a distal end side are formed. Namely, the surface 111*w* is configured by a flat surface 111*f* at the distal end side, and the inclined surface 111*u*. Note that the inclined surface 111*u* is not limited to the linear surface, and may be configured by a curved surface.

Note that angles and positions of the inclined surfaces 111*u* are adjusted so that the eccentric cams 120*i* contact the inclined surfaces 111*u* in the first rotation position in which the respective exposed sites 40*r* are unfixed as shown in FIG. 30, and in the second rotation position that fixes movement of the respective exposed sites 40*r*, the eccentric cams 120*i* contact the flat surfaces 111*f* as shown in FIG. 31.

According to the configuration as above, when the eccentric cam 120*i* rotates from the first rotation position shown in FIG. 30 to the second rotation position shown in FIG. 31, the eccentric cam 120*i* rotates along the inclined surface 111*u*. Thereby, a moving amount in the vertical direction R of the brake member 111 is increased more than that in the case in which the surface 111*w* is configured only by a flat surface even with the same rotation amount of the fixing lever 80. Namely, the braking forces that are given in the vertical direction R to the respective exposed sites 40*r* from the brake members 111 become large.

Accordingly, not only the moving member fixing mechanism 100 can be made compact, but also sufficient fixing forces can be given to the respective exposed sites 40*r* with small rotational forces of the eccentric cams 120*i*. Thereby, the rotation amount of the fixing lever 80 can be reduced, and therefore, the rotation operation of the bending operation knob 9 is prevented from being inhibited by the rotation amount of the fixing lever 80 increasing. Note that the other effects are the same as those in the second to the sixth embodiments described above.

(Eighth Embodiment)

Figure 32:
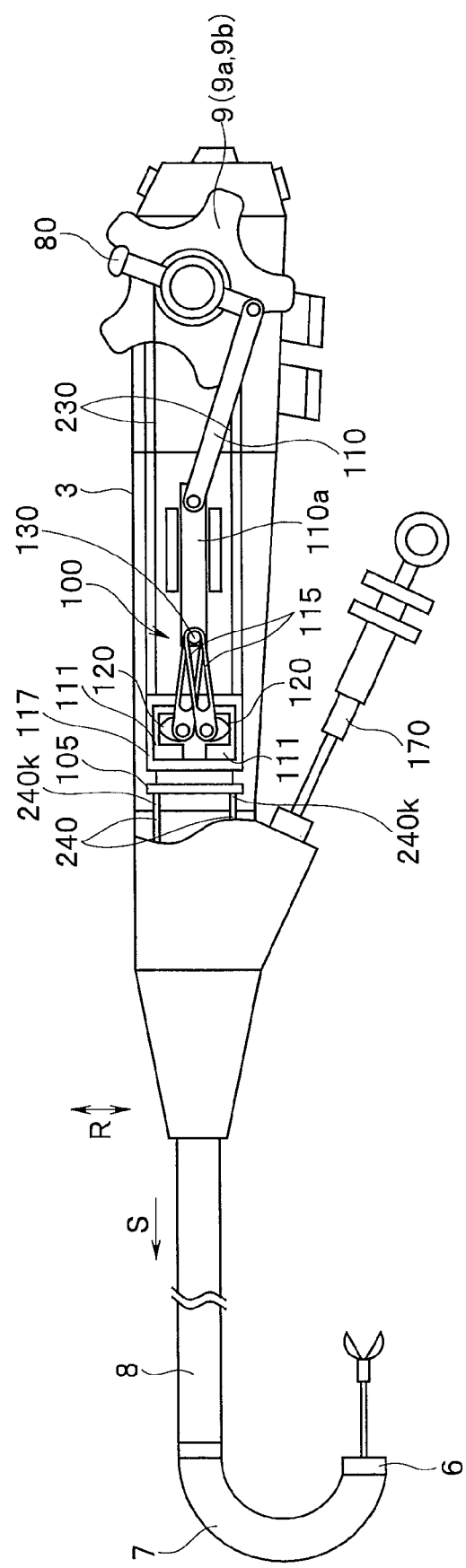
FIG. 32 is a view schematically showing a configuration in which a moving member fixing mechanism is provided in an operation portion of an endoscope of an eighth embodiment with an insertion portion and the operation portion of the endoscope in a state in which inner guide sheaths are unfixed by the moving member fixing mechanism.

FIG. 32 is a view schematically showing a configuration in which a moving member fixing mechanism is provided in an operation portion of an endoscope of the present embodiment in a state in which inner guide sheaths are unfixed by the moving member fixing mechanism, with an insertion portion and the operation portion of the endoscope.

The configuration of the endoscope of the eighth embodiment differs in the point in which the moving member fixing mechanism fixes movement in the insertion direction of wires, as compared with the endoscope of the first embodiment shown in FIG. 1 to FIG. 9, the endoscope of the second embodiment shown in FIG. 10 to FIG. 12, the endoscope of the third embodiment shown in FIG. 13 to FIG. 16, the endoscope of the fourth embodiment shown in FIG. 19 to FIG. 21, the endoscope of the fifth embodiment shown in FIG. 28, the endoscope of the sixth embodiment shown in FIG. 29, and the endoscope of the seventh embodiment shown in FIG. 30 and FIG. 31 that are described above.

Accordingly, only the difference will be described, the similar components to those in the first to the seventh embodiments will be assigned with the same reference signs, and explanation thereof will be omitted. Note that in FIG. 32, a pair of link members of the moving member fixing mechanism 100 will be described with the pair of link members 115 cited as an example.

As shown in FIG. 32, in the present embodiment, the bending portion 7 is configured by a single piece, and a guide sheath with which an outer periphery of a wire 230 that is a moving member is covered is configured by a single coil sheath 240, unlike the first to the seventh embodiments described above.

Further, at proximal ends of the long holes 115*h* of the pair of link members 115, portions that become parallel with the reciprocating portion 110*a* when the braking force becomes the maximum in the second rotation position are provided.

Note that a proximal end 240*k* of the coil sheath 240 with the wire 230 being inserted through an inside thereof is fixed to the stop member 105.

Further, the respective brake members 111 have sections formed into U-shapes. The respective brake members 111 simultaneously fix movement of the exposed sites in the space 117*v* in the guide member 117, in the respective wires 230.

According to the configuration as above, in the conventional endoscope in which only the single bending portion 7 is provided, configurations that make the force which stops the rotation of the up-and-down bending operation knob 9*a* and the left-and-right bending operation knob 9*b* gradually increase are used and are provided separately for the respective knobs 9*a* and 9*b* respectively, for the engaging mechanisms that bring rotation of the bending operation knob 9 of the operation portion 3 into a semi-fixed state (a state in which the bending portion can be bent, but a force is needed for rotation of the bending operation knob 9, and therefore, the bending portion 7 can be bent slowly). Therefore, when the bent shape of the bending portion 7 is to be kept in the semi-fixed state in all of the four directions that are an up, a down, a left and a right, knobs or levers for semi-fixing in the each engaging mechanism need to be rotationally operated, and the operation is complicated.

Further, when the bending portion 7 is given a force by hitting against the wall in a body cavity, the treatment instrument 170 being inserted, or the like, the bending portion 7 sometimes moves, because chains are located between portions that connect the sprockets of the bending operation knob 9 and the respective wires 230.

Therefore, when the bending state of the bending portion 7 is desired to be firmly fixed at the time of treatment and the like, the surgeon needs to keep holding the bending operation knob 9 with his or her finger.

However, according to the configuration of the present embodiment, movement in the insertion direction S of the respective wires 230 can be reliably fixed with use of the moving member fixing mechanism 100, and therefore, a desired bent shape of the bending portion 7 is not semi-fixed, but can be firmly fixed with use of the fixing lever 80.

Therefore, such an event can be prevented that the bending angle of the bending portion 7 changes by the distal end of the treatment instrument 170 receiving the force from a body wall, and treatment becomes difficult, at the time of the treatment of dissecting the inside of a body cavity by pushing and drawing of the treatment instrument 170, and the like.

Furthermore, since the mechanisms that semi-fix the rotation of the respective knobs 9*a* and 9*b* become unnecessary, a standing height of the bending operation knob 9 can be made low, and therefore, the bending operability of surgeons with small hands is especially enhanced.

Further, even for surgeons with hands in an average size, it is a difficult operation to operate the two superimposed bending knobs (in general, the one on the upper side is a knob that bends the bending portion to the left and the right, and the one on the lower side is a knob that bends the bending portion up and down) simultaneously with left fingers that hold the operation portion, but since the height of the knob can be made low, bending operability is enhanced.

Note that the other effects are the same as those in the first to the seventh embodiments described above.

Further, with use of the moving member fixing mechanism 100 of the present embodiment, the movement of the respective wires 230 is not completely fixed, but the braking forces that are given to the respective wires 230 from the respective brake members 111 are decreased, whereby a semi-fixed state of the bending portion 7 may be realized similarly to the conventional apparatus.

(Ninth Embodiment)

Figure 33:
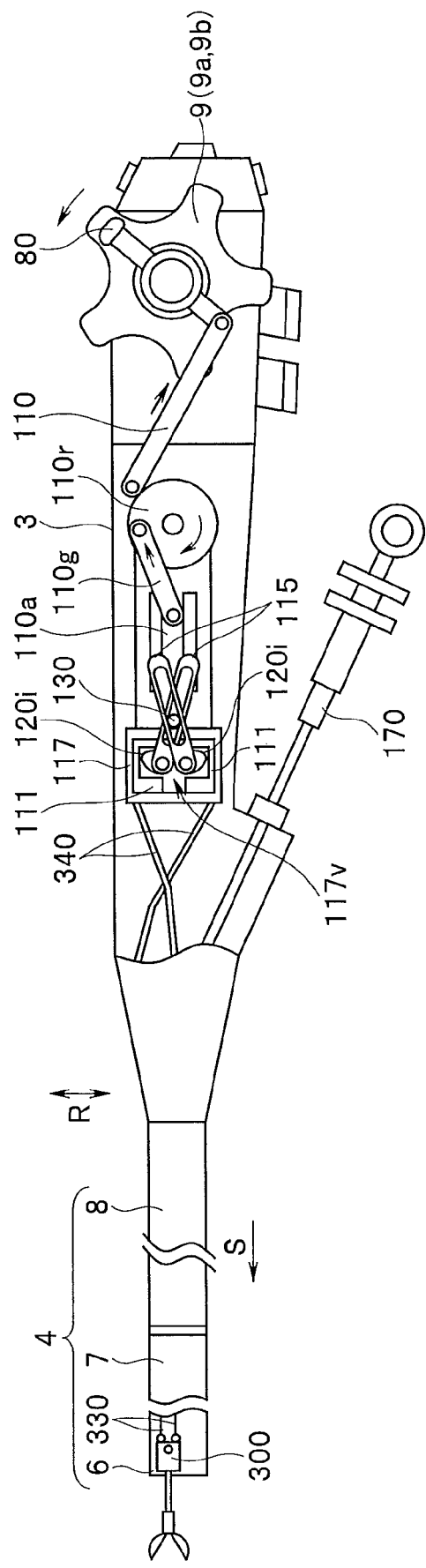
FIG. 33 is a view schematically showing a configuration in which a moving member fixing mechanism is provided in an operation portion of an endoscope of a ninth embodiment with an insertion portion and the operation portion of the endoscope in a state in which guide sheaths are unfixed by the moving member fixing mechanism.
Figure 34:
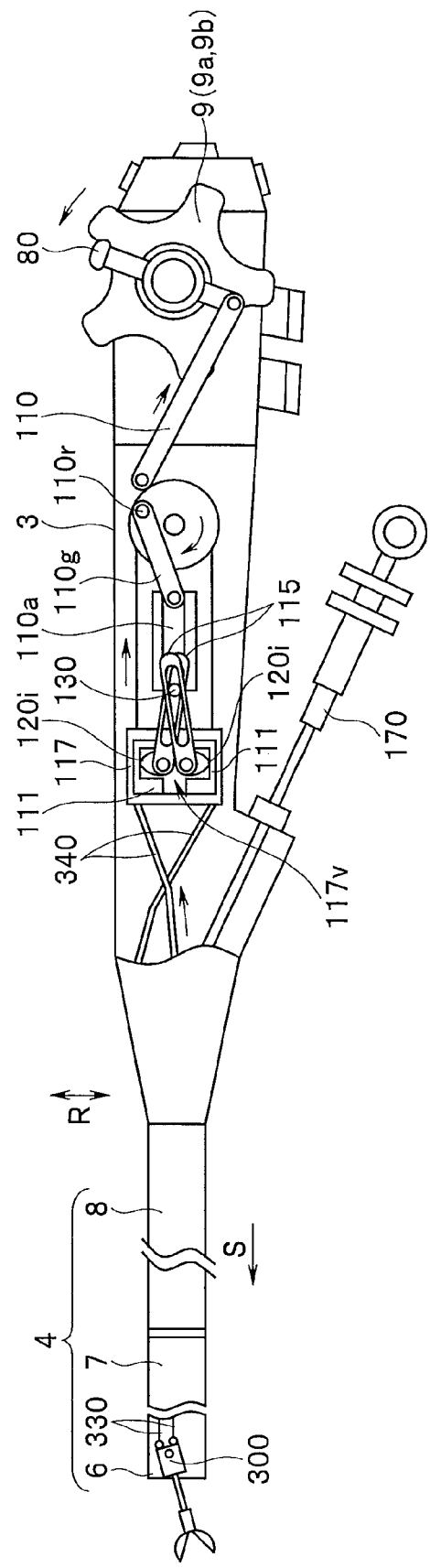
FIG. 34 is a view schematically showing a state in which the guide sheaths are fixed by the moving member fixing mechanism of FIG. 33, with the insertion portion and the operation portion of the endoscope.

FIG. 33 is a view schematically showing a configuration in which a moving member fixing mechanism is provided in an operation portion of an endoscope of the present embodiment in a state in which guide sheaths are unfixed by the moving member fixing mechanism, with an insertion portion and the operation portion of the endoscope. FIG. 34 is a view schematically showing a state in which the guide sheaths are fixed by the moving member fixing mechanism of FIG. 33, with the insertion portion and the operation portion of the endoscope.

The configuration of the endoscope of the ninth embodiment differs in the point in which the moving member fixing mechanism fixes movement of the wire that raises a forceps raising stand, as compared with the endoscope of the first embodiment shown in FIG. 1 to FIG. 9, the endoscope of the second embodiment shown in FIG. 10 to FIG. 12, the endoscope of the third embodiment shown in FIG. 13 to FIG. 16, the endoscope of the fourth embodiment shown in FIG. 19 to FIG. 21, the endoscope of the fifth embodiment shown in FIG. 28, the endoscope of the sixth embodiment shown in FIG. 29, the endoscope of the seventh embodiment shown in FIG. 30 and FIG. 31, and the endoscope of the eighth embodiment shown in FIG. 32 that are described above.

Accordingly, only the difference will be described, the similar components to those in the first to the eighth embodiments will be assigned with the same reference signs, and explanation thereof will be omitted. Note that in FIG. 33 and FIG. 34, the pair of link members of the moving member fixing mechanism 100 will be described with the pair of link members 115 cited as an example.

In the distal end portion 6 of the endoscope 2, a forceps raising stand 300 that is an action portion is rotatably provided. Note that a periphery around a distal end of the forceps raising stand 300 is water-tightly covered with a rubber cover except for a channel outlet.

To the forceps raising stand 300, distal ends of two raising operation wires (hereinafter, simply called wires) 330 that are moving members are connected, and proximal ends of the respective wires 330 are wound around a drum 110r.

Note that to the drum 110r, the crank member 110 connected to the fixing lever 80 is connected, and it is configured such that with rotation of the fixing lever 80, the drum 110r rotates via the crank member 110 to pull and slacken the respective wires 330, whereby the forceps raising stand 300 rotates.

Further, to a distal end of the crank member 110, a proximal end of a connection member 110g is rotatably connected, and a distal end of the connection member 110g is rotatably connected to a proximal end of the reciprocating portion 110a.

Outer peripheries of the respective wires 330 are covered with respective raising wire guide sheaths 340, proximal end sides of the respective wires 330 penetrate through the guide member 117 of the moving member fixing mechanism 100 along the insertion direction S, and parts thereof are exposed to the space 117v.

Note that the respective raising wire guide sheaths 340 cross each other in the operation portion 3, and respective proximal ends are fixed to the guide member 117.

Note that movement in the insertion direction S of exposed sites in the space 117v, of the respective wires 330, is made simultaneously fixable, by movement in the vertical direction R of the respective brake members 111 with rotation of the fixing lever 80, as shown in FIG. 34.

Next, an operation of the present embodiment will be described.

As shown in FIG. 33, when in the first rotation position where the respective brake members 111 are separated from the exposed sites of the respective wires 330, the fixing lever 80 is rotated counterclockwise, the drum 110r is rotated clockwise via the crank member 110 to raise the forceps raising stand 300, and thereafter, the fixing lever 80 is further rotated counterclockwise, the drum 110r is further rotated clockwise via the crank member 110 to move the reciprocating portion 110a rearward via the connection member 110g connected to the drum 110r, whereby the pair of link members 115 are brought into an opened state by the slider pin 130, as shown in FIG. 34.

From the above, by rotation of the respective eccentric cams 120i, the respective brake members 111 press the exposed sites in the space 117v, of the respective wires 330 to the wall surfaces 117w of the guide member 117, whereby movement is fixed in the insertion direction S of the respective wires 330. Namely, a rising angle of the forceps raising stand 300 is fixed.

According to the configuration as above, a raising operation of the forceps raising stand 300 and a fixing operation of the rising angle of the forceps raising stand 300 can be performed with the single fixing lever 80. Therefore, the number of components can be reduced, and downsizing of the operation portion 3 can be achieved.

Note that the other effects are the same as those in the first to the eighth embodiments described above.

Note that hereinafter, a modification will be shown. In the first to the ninth embodiments described above, it is shown that the bending portion 7 is provided at the distal end side of the insertion portion 4, but the bending portion 7 may be provided at any position of the insertion portion 4 without being limited thereto.

Further, in the first to the ninth embodiments described above, the insertion apparatus is shown with the endoscope 2 cited as an example, but the insertion apparatus is not limited to the endoscope 2, and may be applicable to other insertion apparatuses such as a guide tube, various treatment instruments, and a manipulator if only the apparatuses have action portions that act by operation input from the operation portions 3, at the distal ends of the insertion portions 4.

Figure 35:
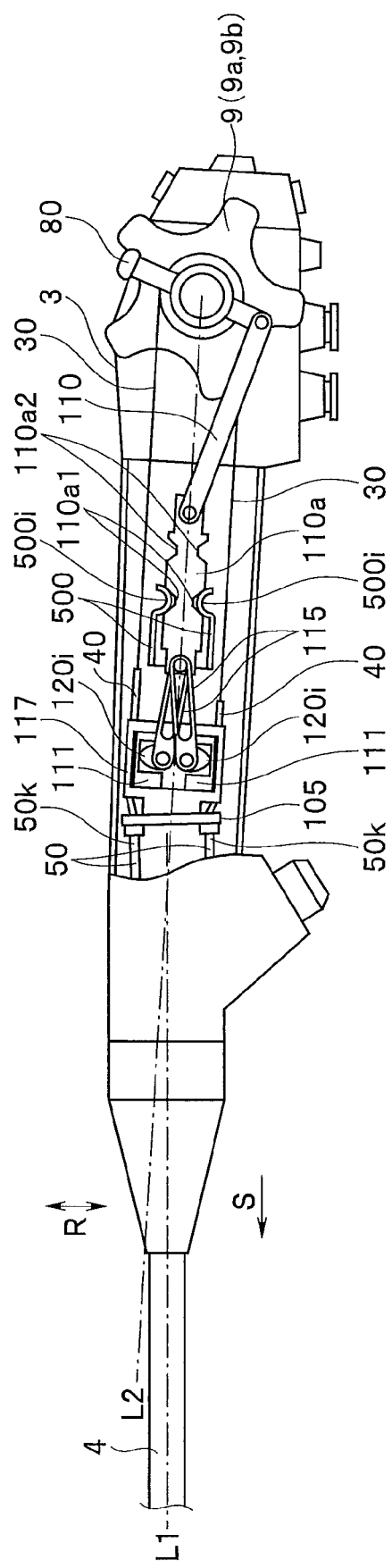
FIG. 35 is a view showing a configuration in which a click leaf spring is provided at the moving member fixing mechanism, with the insertion portion and the operation portion of the endoscope.

FIG. 35 is a view showing a configuration in which a click leaf spring is provided at a moving member fixing mechanism, with an insertion portion and an operation portion of an endoscope.

Incidentally, in the present embodiment described above, the structure that fixes the stop member 105 to the structure body of the operation portion 3 is included, but in the configuration shown in FIG. 35, the stop member 105 that fixes the proximal ends 50k of the respective outer guide sheaths 50 is fixed to the guide member 117 of the moving member fixing mechanism 100.

Further, depending on the kind of an endoscope, for the purpose of enhancement of operability and insertability of the insertion portion, the proximal end of the insertion portion 4 is connected to the operation portion 3 in a state in which an axis L1 in a longitudinal direction of the insertion portion 4 is inclined slightly, for example, at about 3° with respect to an axis L2 in a longitudinal direction of the operation portion 3, as shown in FIG. 35. Thereby, in the configuration like this, the stop member 105 is fixed to the guide member 117 to be substantially perpendicular to the axis L1 to avoid interference with an inner wall of an exterior member that configures a grasping portion of the operation portion 3.

Further, in side surfaces along the insertion direction S of the reciprocating portion 110a of the crank member 110, V-shaped grooves 110a1 and 110a2 are respectively formed at a distal end side and a proximal end side. Namely, on the side surfaces, four V-shaped grooves are formed. Note that in both the side surfaces, distances between the V-shaped grooves 110a1 and the V-shaped grooves 110a2 in the insertion direction S are the same as the moving amount in the insertion direction S of the reciprocating portion 110a.

Further, in the moving member fixing mechanism 100, a pair of click leaf springs 500, which have fitting portions 500i that are folded into semi-circular shapes at proximal ends thereof, are provided.

Note that the other configurations are the same as those of the first to the ninth embodiments described above.

In the configuration as above, the respective outer guide sheaths 50 are inclined with respect to the axis L2. Thereby, the respective inner guide sheaths 40 that are inserted through the insides of the respective outer guide sheaths 50 are guided obliquely along the axis L1 to the above described through-holes 117x that are formed in the guide member 117.

Note that inclined angles of the respective inner guide sheaths 40 are very small, and therefore, the respective inner guide sheaths 40 move smoothly in the guide member 117.

As shown in FIG. 35, when the fixing lever 80 is rotationally operated counterclockwise, and the respective eccentric cams 120i are moved to the second rotation position from the first rotation position to fix the movement of the inner guide sheaths 40, the reciprocating portion 110a moves rearward. Thereby, the fitting portions 500i of the pair of click leaf springs 500 are respectively fitted in a pair of V-shaped grooves 110a1 of the reciprocating portion 110a. With the fitting, click sensing is transmitted to the fingers of the surgeon who operates the fixing lever 80 via the fixing lever 80.

Next, when the fixing lever 80 is rotationally operated clockwise, and the respective eccentric cams 120i are moved to the first rotation position from the second rotation position to release fixation of the movement of the inner guide sheaths 40, the reciprocating portion 110a moves forward. Thereby, the fitting portions 500i of the pair of click leaf springs 500 are respectively fitted in a pair of V-shaped grooves 110a2 of the reciprocating portion 110a. With the fitting, click sensing is transmitted to the fingers of the surgeon who operates the fixing lever 80 via the fixing lever 80.

According to the configuration like this, the stop member 105 is fixed obliquely, more specifically, substantially orthogonally to the axis L1, in the operation portion 3, and therefore, interference with the inner wall of the exterior member that configures the grasping portion of the operation portion can be avoided.

Further, since axial deviations between the through-holes 117x provided in the guide member 117 and the centers of the respective outer guide sheaths 50 (the centers of the respective inner guide sheaths 40) can be reduced when the stop member 105 is fixed to the guide member 117 than when the stop member 105 is fixed to the structure body of the operation portion 3, sliding resistances of the respective inner guide sheaths 40 in the through-holes 117x can be reduced.

Further, since the surgeon can know the switching positions of fixing and unfixing of the respective inner guide sheaths 40 by click sensing, the surgeon does not stop the rotational operation of the fixing lever 80 halfway, and therefore, the surgeon can perform a reliable switching operation.

Note that in the present configuration, the click leaf spring 500 is used to transmit click sensing to the surgeon, but this is not restrictive, and a ball plunger may be provided instead of a leaf spring. Furthermore, the V-shaped grooves may be provided at the rotary plate of the fixing lever 80, for example, without being limited to the reciprocating portion 110a.

What is claimed is:

1. An insertion apparatus, comprising:
an insertion portion that is inserted into a subject;
an action portion that is provided at the insertion portion;
moving members that are provided to move in a direction in which the insertion portion is inserted, in an inside of the insertion portion, to cause the action portion to act;
an operation member that is for operating the action portion by an operator;
a guide member that has inner circumferential faces configured by wall surfaces provided along a direction in which the moving member moves;
a crank member that has a reciprocating portion that moves forward and rearward in the direction in which the insertion portion is inserted, with an operation of the operation member;
a pair of link members that open and close with a pin provided at the reciprocating portion of the crank member as a center, with movement of the crank member; and
cam members that are provided in an inside of the guide member, and respectively connected to one ends of the link members to be rotated therewith, the cam members including a pair of eccentric cams that rotate to a second rotation position where the cam members simultaneously press the moving members that penetrate through the inside of the guide member with a pressing force toward the wall surfaces of the guide member in a perpendicular direction orthogonal to the direction in which the insertion portion is inserted, and a first rotation position where the cam members are separated from the moving members, by either one of opening and closing of the link members;
wherein the pair of link members cross each other, and the pin is fitted into a crossing site in long holes that are formed respectively along axial directions of the link members to penetrate through the respective long holes, and
the link members open and close by forward and rearward movement in the direction in which the insertion portion is inserted, of the crossing site, by the pin in the long holes moving forward and rearward in the direction in which the insertion portion is inserted, with the reciprocating portion of the crank member moving forward and rearward in the direction in which the insertion portion is inserted.

2. The insertion apparatus according to claim 1, wherein the action portion is a bending portion that configures a part of the insertion portion and is bendable in a plurality of directions.

3. The insertion apparatus according to claim 2, further comprising:
a wire that has a distal end in the direction in which the insertion portion is inserted connected to the bending portion, and causes the bending portion to bend by being moved forward and rearward in the direction in which the insertion portion is inserted;
an inner guide sheath that is provided in the insertion portion, has the wire inserted through an inside to freely advance and retract with respect to the direction in which the insertion portion is inserted, and has a distal end in the direction in which the insertion portion is inserted fixed to an intermediate position in the direction in which the insertion portion is inserted, of the bending portion; and
an outer guide sheath that is provided in the insertion portion, has a distal end in the direction in which the insertion portion is inserted fixed to a distal end of a flexible tube portion which is connectively provided on a proximal end side of the bending portion in the direction in which the insertion portion is inserted, has a proximal end in the direction in which the insertion portion is inserted fixed in a rear side in the direction in which the insertion portion is inserted from the flexible tube portion, and has the inner guide sheath inserted through an inside to freely advance and retract with respect to the direction in which the insertion portion is inserted,
wherein the moving member is the inner guide sheath.

4. The insertion apparatus according to claim 1, wherein the cam member applies a pressing force to the moving member outwardly toward the wall surface of the guide member in a direction orthogonal to the direction in which the insertion portion is inserted.

5. An insertion apparatus, comprising:
an insertion portion that has a distal end and a proximal end, and is inserted into a subject;
an action portion that is provided at a distal end side of the insertion portion;
an operation portion that is provided on a proximal end side of the insertion portion, for operating the insertion portion;
a pair of moving members that are inserted through the operation portion and the insertion portion, and are moved along a longitudinal axis direction of the insertion portion, the moving members being connected with the action portion;
an operation knob that is provided at the operation portion and causes the action portion to act by moving the moving members;
a lever that is provided at the operation portion and is different from the operation knob;
a reciprocating portion that is capable of reciprocating along an insertion direction of the insertion portion in accordance with an operation of the lever;
a first member that is provided in the operation portion to have a first longitudinal axis defined and two end portions, extends along the first longitudinal axis by a predetermined length, and has a first long hole formed along the first longitudinal axis;
a second member that is provided in the operation member to cross the first member and to have a second longitudinal axis defined and two end portions, extends long the second longitudinal axis by a predetermined length, and has a second long hole formed along the second longitudinal axis;
a first camshaft that is provided at one end side of the first member and securely support the first member to be rotatable with respect to the operation portion;
a second camshaft that is provided at one end side of the second member and securely supports the second member to be rotatable with respect to the operation portion, the second camshaft being different from the first camshaft;
a pin that is provided at the reciprocating portion as to penetrate the first long hole and the second long hole at a crossing position of the first member and the second member, and moves in the first and second long holes by movement of the reciprocating portion based on the operation of the lever, to thereby rotate the first and second members and change a crossing angle of the first member and the second member;
a first wall surface that is arranged in the operation portion such that one of the pair of moving members is located between the first camshaft and the first wall surface;
a second wall surface that is arranged in the operation portion such that other of the pair of moving members is located between the second camshaft and the second wall surface;
a first pressing portion that has a first cam which is fixed at one end side of the first member and rotates with the first member about the first camshaft as a center, and when the first member is rotated by the movement of the pin such that the crossing angle of the first member and the second member decreases, changes a force of rotating the first cam into a force acting in a direction different from a moving direction of the moving member, to thereby press the moving member toward the first wall surface and suppress the movement of the moving member; and
a second pressing portion that has a second cam which is fixed at one end side of the second member and rotates with the second member about the second camshaft as a center, and when the second member is rotated by the movement of the pin such that the crossing angle of the first member and the second member decreases, changes a force of rotating the second cam into a force acting in a direction different from a moving direction of the moving member, to thereby press the moving member toward the second wall surface and suppress the movement of the moving member.

6. The insertion apparatus according to claim 5,
wherein the first cam of the first pressing portion includes a first eccentric cam that presses the moving member toward the first wall surface by the lever action with the first camshaft as a fulcrum, the crossing point of the first member and the second member where the pin is located as a power point and a contact portion of the first eccentric cam and the moving member as a point of action when the first member is rotated, and
the second cam of the second pressing portion includes a second eccentric cam that presses the moving member toward the second wall surface by the lever action with the second camshaft as a fulcrum, the crossing point of the first member and the second member where the pin is located as a power point and a contact portion of the second eccentric cam and the moving member as a point of action when the second member is rotated.

7. The insertion apparatus according to claim 6,
wherein a distance between the first camshaft and an outer periphery of the first eccentric cam is set to be shorter than a distance between the first camshaft and the pin, and a distance between the .second camshaft and an outer periphery of the second eccentric cam is set to be shorter than a distance between the second camshaft and the pin, and
the pin moves in the first and second long holes so that the crossing angle of the first member and the second member is decreased to elongate a distance between the fulcrum and the power point and increase the lever action, and thereby forces of rotating the first and second members are converted into forces of pressing the moving members by the first eccentric cam and the second eccentric cam.

8. The insertion apparatus according to claim 5,
wherein the first pressing portion includes a first brake member that intervenes between the first cam and the moving member to be contactable with the moving member, and when the first cam is rotated by the movement of the pin such that the crossing angle of the first member and the second member is decreased, moves in the direction different from the moving function of the moving member and presses the moving member toward the first wall surface, and
the second pressing portion includes a second brake member that intervenes between the second cam and the moving member to be contactable with the moving member, and when the second cam is rotated by the movement of the pin such that the crossing angle of the first member and the second member is decreased, moves in the direction different from the moving direction of the moving member and press the moving member toward the second wall surface.

9. The insertion apparatus according to claim 8,
wherein the first cam includes a first eccentric cam that presses the moving member toward the first wall surface by the first brake member by the lever action with the first camshaft as a fulcrum, the crossing point of the first member and the second member where the pin is located as a power point and a contact portion of the first eccentric cam and the first brake member as a point of action when the first member is rotated, and the second cam includes a second eccentric cam that presses the moving member toward the second wall surface by the second brake member by the lever action with the second camshaft as a fulcrum, the crossing point of the first member and the second member where the pin is located as a power point and a contact portion of the second eccentric cam and the second brake member as a point of action when the second member is rotated.

10. The insertion apparatus according to claim 9,
wherein distances between the first and second camshafts and outer peripheries of the first and second eccentric cams are set to be shorter than distances between the first and second camshafts and the pin, and thereby forces of rotating the first and second members are converted into forces of pressing the first brake member and the second brake member by the first eccentric cam and the second eccentric cam, respectively, by the lever action.

\* \* \* \* \*

UNITED STATES PATENT AND TRADEMARK OFFICE
CERTIFICATE OF CORRECTION

PATENT NO. : 9,615,727 B2
APPLICATION NO. : 14/042894
DATED : April 11, 2017
INVENTOR(S) : Keiichi Arai et al.

It is certified that error appears in the above-identified patent and that said Letters Patent is hereby corrected as shown below:

In the Claims

Column 38, Line 37 (Claim 7, Line 5) should read:
and a distance between the second camshaft and an Column 39, Line 6 (Claim 9, Line 6) should read:
first member and the second member where the pin is Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*